United States Patent
Dohata et al.

(10) Patent No.: US 10,653,335 B2
(45) Date of Patent: May 19, 2020

(54) MAGNETIC RESONANCE IMAGING DEVICE AND RF COIL ASSEMBLY WITH MATCHING SWITCH CIRCUIT AND TUNING SWITCH CIRCUIT

(71) Applicant: HITACHI, LTD., Tokyo (JP)

(72) Inventors: Masayoshi Dohata, Tokyo (JP); Yoshihisa Soutome, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 946 days.

(21) Appl. No.: 14/897,669

(22) PCT Filed: Jun. 23, 2014

(86) PCT No.: PCT/JP2014/066564
§ 371 (c)(1),
(2) Date: Dec. 11, 2015

(87) PCT Pub. No.: WO2014/208501
PCT Pub. Date: Dec. 31, 2014

(65) Prior Publication Data
US 2016/0135711 A1  May 19, 2016

(30) Foreign Application Priority Data
Jun. 26, 2013 (JP) .................. 2013-133283

(51) Int. Cl.
*A61B 5/055* (2006.01)
*G01R 33/34* (2006.01)
*G01R 33/36* (2006.01)

(52) U.S. Cl.
CPC ...... *A61B 5/0555* (2013.01); *G01R 33/34084* (2013.01); *G01R 33/3628* (2013.01); *G01R 33/3664* (2013.01)

(58) Field of Classification Search
CPC .............. A61B 5/0555; G01R 33/3664; G01R 33/34084; G01R 33/3628
See application file for complete search history.

(56) References Cited

U.S. PATENT DOCUMENTS 5,543,712 A * 8/1996 Arakawa ............ G01R 33/3628
324/318
5,670,881 A   9/1997 Arakawa et al.
(Continued)

FOREIGN PATENT DOCUMENTS

JP     63-65408 U    4/1988
JP     3-45246 A     2/1991
(Continued)

OTHER PUBLICATIONS

International Preliminary Report on Patentability received in corresponding International Application No. PCT/JP2014/066564 dated Jan. 7, 2016.
(Continued)

*Primary Examiner* — Serkan Akar
(74) *Attorney, Agent, or Firm* — Mattingly & Malur, PC

(57) ABSTRACT

In a magnetic resonance imaging device provided with a deformable RF coil permanently mounted on a patient table, the RF coil can constantly maintain a matching state and a tuned state in a state of being flat on a top plate and in a state of being wound around a test object. Coil-side connectors 306-2 and 306-3 provided in a deformable RF coil 300 form a detector in cooperation with any one of fixture-side connectors 506-1 to 506-6, in which the detector detects a fitted state therebetween. A tuning circuit and a matching circuit of coil elements of the RF coil 300 are switched by an output of the detector to change tuning and matching
(Continued)

parameters, and to maintain a matching state and a tuned state with respect to a state change indicating that the RF coil 300 is in a wound state.

8 Claims, 16 Drawing Sheets

(56) References Cited

U.S. PATENT DOCUMENTS

| | | | | |
|---|---|---|---|---|
| 6,054,858 | A * | 4/2000 | Dumoulin | G01R 33/3628 324/314 |
| 2009/0009172 | A1 | 1/2009 | Feld et al. | |
| 2009/0015256 | A1 * | 1/2009 | Bottomley | G01R 33/3415 324/309 |

FOREIGN PATENT DOCUMENTS

| | | |
|---|---|---|
| JP | 3-264053 A | 11/1991 |
| JP | 2003-010146 A | 1/2003 |
| JP | 2006-6400 A | 1/2006 |
| JP | 3816618 B2 | 6/2006 |
| JP | 2007-530972 A | 11/2007 |
| JP | 2008-178453 A | 8/2008 |
| JP | 2009-011836 A | 1/2009 |

OTHER PUBLICATIONS

International Search Report of PCT/JP2014/066564.
P. B. Roemer et al., "The NMR Phased Array", Magnetic Resonance in Medicine, 1999, pp. 192-225, vol. 16.

* cited by examiner (a)

(b)

(a)

(b)

(a)

(b)

(c)

(a)

(b)

MAGNETIC RESONANCE IMAGING DEVICE AND RF COIL ASSEMBLY WITH MATCHING SWITCH CIRCUIT AND TUNING SWITCH CIRCUIT

TECHNICAL FIELD

The invention relates to a magnetic resonance imaging device (MRI apparatus), and more particularly, to a radio frequency coil (RF coil) used on a patient table and a fixture therefor.

BACKGROUND ART

An MRI apparatus is an apparatus that applies a gradient magnetic field and an excitation radio frequency magnetic field to a subject disposed in a uniform static magnetic field space in a shield room, receives a nuclear magnetic resonance signal generated using a nuclear magnetic resonance phenomenon by a radio frequency coil (RF reception coil), and images a test object. A range capable of being simultaneously imaged is limited to the range of the static magnetic field space at most, and a range where high image quality is obtained is limited to the sensitivity range of the RF reception coil.

As performance characteristics which are necessary in the RF reception coil, there are SN ratio for high image quality, wide sensitivity range for wide-field imaging, parallel imaging performance for high speed imaging, and the like. The parallel imaging is a method for simultaneously performing signal measurement using a reception coil formed by plural coil elements to reduce an imaging time. Plural rectangular or circular loop-shaped coil elements are arranged in a certain direction (a body width direction or a body length direction), and a phase encoding direction is set along the direction. In this technique, if the arrangement of the coil elements is optimal, it is possible to reduce the imaging time to the time divided by the number of the coil elements arranged in the phase encoding direction. Further, by two-dimensionally arranging the plural loop-shaped coil elements (for example, in the body width direction or the body length direction), it is possible to realize a reception coil capable of achieving higher-speed imaging and having a sensitivity region in a wide range such as the whole body.

In order to realize excellent parallel imaging, it is necessary that electromagnetic coupling between the plural loop-shaped coil elements is sufficiently small. This is because if the electromagnetic coupling between the coil elements is present, noise interference occurs between the coil elements, and thus, the SN ratio of an image deteriorates. In order to solve such a problem, in a method disclosed in NPL 1, magnetic coupling that occurs between elements is suppressed by using an amplifier with low input impedance and a capacitor connected to each element for signal detection and amplification. According to this method, if the distance between two coil elements is long to a certain degree, it is possible to reduce the electromagnetic coupling between two coil elements to a degree without a practical problem. Here, when the loop size of the coil element is large with respect to the distance between two coil elements, the magnetic coupling cannot be suppressed by only the method disclosed in NPL 1. In this case, by appropriately overlapping two adjacent coil elements (about 10% in area), it is possible to remove the magnetic coupling between the coil elements. When the degree of overlapping is not appropriate, a resonance point of input impedance of the coils is divided into two or more because of inductive coupling between the coil elements. When the electromagnetic coupling between two coil elements is large as the resonance point of input impedance of the coils is divided into two or more, the magnetic coupling cannot be suppressed, even using the method disclosed in NPL 1. Accordingly, in reality, it is preferable that coupling is reduced to a sufficiently small degree by using the method disclosed in NPL 1 and the overlapping method together. Further, by connecting in series an auxiliary coil to each of two coils for which coupling is to be reduced, it is possible to remove inductive coupling between coils.

The above description is mainly made with respect to the RF reception coil that receives a nuclear magnetic resonance signal, but the same coil structure may be realized with respect to an RF transmitting coil for application of a radio frequency magnetic field. In the case of the transmitting coil, a power amplifier with low output impedance and a pulse generator (transmission modulator), instead of a low noise amplifier with low input impedance for signal detection and amplification and a receiver, are connected to the RF coil. As performance characteristics which are necessary in the transmitting coil, there are high emission efficiency for a low specific absorption rate (SAR), uniform magnetic field generation performance, and the like. For this purpose, by supplying radio frequency magnetic fields having different amplitudes and phases to plural coil elements, or by controlling an element that supplies a radio frequency magnetic field so that only a desired portion is irradiated with an excitation magnetic field, it is possible to make an excitation magnetic field distribution for a subject uniform, or to reduce the specific absorption rate (SAR). Such a technique is referred to as RF shimming or parallel transmission. In this case, similar to the case of the reception coil, it is necessary that electromagnetic coupling between coil elements is sufficiently small. In consideration of different forms of use of a coil that includes plural elements, if a transmitter-receiver switching circuit is used between a reception amplifier, a transmission amplifier, and the coil, it is possible to use the coil as a RF coil used both as transmission coil and reception coil. Accordingly, since the following description relates to a coil capable of being used as a transmitting coil, and also, as a reception coil, an "RF coil" is used as a term including two meanings of the "RF reception coil" and the "RF transmitting coil".

However, when testing a wide range all at once, a wide range RF coil in which the plural loop-shaped coil elements as described above are two-dimensionally arranged (for example, in the body width direction and the body length direction) to widen a sensitivity range is used. Further, when testing a local range such as a head or a shoulder with high definition, an RF coil dedicated to each portion (dedicated to the head in the case of the head, or dedicated to a shoulder joint in the case of the shoulder) is used. Even in the case of the RF coil dedicated to each portion, the RF coil includes plural coil elements, and the coil elements are provided in a unit having a shape dedicated to a portion of the subject to be imaged, and are optimally arranged therein so that electromagnetic coupling is suppressed to the minimum.

The wide range RF coil and the RF coil dedicated to each portion as described above are appropriately set on a top plate by an operator at every instance of imaging, in the related art. It is necessary that the operator carries the RF coil and correctly aligns a subject and the RF coil at every instance of imaging. Particularly, in the case of the RF coil having the above-described wide sensitivity range, since the size is large and the weight is heavy, the workload of the operator who carries the RF coil is increasing. Further, when a positional relationship between the subject and the coil is not correct, it is necessary to separate the subject from the coil and to perform resetting.

From such a background, as requirements for the RF coil, a requirement of enhanced usability is increased in addition to requirements such as high image quality, high speed imaging, a low SAR, or uniform emission magnetic field control, and there is demand for an RF coil in which coil setting at every instance of imaging is unnecessary. Further, as disclosed in PTL 1, an RF coil that is permanently mounted on a cradle (a stand or a top plate) that covers a subject or is built in the cradle has been proposed. Further, a whole body photographing method that employs parallel imaging and table movement together has been used. Since the RF coil used in such a case is an RF coil which is formed by arranging plural stereoscopic elements such as saddle coils disclosed in PTL 1 or two-dimensionally arranging the above-mentioned loop shaped coil elements, and has a wide sensitivity range. The wide range RF coil that includes the plural elements is permanently mounted on a table, and a part of the elements is appropriately selected and controlled so as to be operated after moving to the position of the cradle and the position of the center of a magnetic field. Thus, it is possible to image a wide range such as the whole body in a seamless manner. Further, in the case of the RF coil dedicated to each portion, if the RF coil is permanently mounted at a determined position on the cradle together with the wide range RF coil, similarly, by appropriately selecting and controlling an element present at the position of the top plate and the position of the center of the magnetic field, it is possible to perform imaging in a seamless manner. In both cases, a "lower coil" disposed under a subject in a body thickness direction is built in the cradle, or is permanently mounted in the cradle, and thus, a patient setting time is reduced.

Further, when setting a subject in the RF coil that is permanently mounted in the cradle, in the case of the "lower coil" disposed under the subject in the body thickness direction, it is possible to set the subject with the "lower coil" being permanently mounted. However, in the case of an "upper coil" disposed above the subject in the body thickness direction, the "upper coil" becomes an obstruction in setting the subject. Thus, when setting of the subject, by employing a structure in which the "upper coil" and the "lower coil" are separated or the "upper coil" slides with respect to the "lower coil", it is possible to easily perform the setting of the patient and the coil.

The above-described RF coil is configured so that its shape is not changed, but in order to realize a higher SN ratio or emission efficiency, a flexible structure such that the coil is in contact with a subject may be used. In the related art, in order to enhance convenience when setting a patient, even in the case of a lower coil of a permanently mounted wide range RF coil being used in a flat shape, if a part thereof is formed as a flexible structure, it is advantageous to wind the coil around a subject according to each portion to be imaged. Further, if the RF coil dedicated to each portion is formed as a flexible structure, it is possible to perform imaging with respect to a movement of a joint or the like as an imaging object, and even when the size of the imaging object becomes different, it is possible to perform imaging in a coil shape of being constantly in contact therewith. In performing imaging using the RF coil having such a flexible structure, in order to obtain an image of higher image quality, a patient fixture belt for fixing a positional relationship between the coil and a subject is used. PTL 2 discloses a fixing belt for fixing a subject on a table (bed), in which an RF coil is disposed to be at least partially assembled with the fixing belt. Further, the RF coil assembled with the fixing belt is coupled with an electronic device in the table by conductive coupling, or is coupled with the electronic device in the table by capacitive coupling or inductive coupling, and thus, convenient patient setting is realized. Further, PTL 3 discloses a structure in which a lower coil that is permanently mounted on a top plate on a table is at least partially deformable with respect to a subject placed on the lower coil so as to select an imaging position and a non-imaging position. Thus, in imaging, the subject and the coil are in contact with each other to realize a high SN ratio, and in non-imaging, the lower coil becomes flat so that setting of the subject is easily performed.

Generally, a transmitting coil generates a reflected wave if matching between the transmitting coil and a load is not sufficient, and thus, its emission efficiency is lowered. PTL 4 discloses a technique for solving the problem. In this technique, plural capacitor banks are provided to be respectively switched, and even when a load varies, reflection is suppressed to prevent reduction in emission efficiency.

CITATION LIST

Patent Literature

PTL 1: JP-A-2003-10146
PTL 2: JP-A-2009-11836
PTL 3: JP-A-2008-178453
PTL 4: Japanese Patent No. 3816618
PTL 5: JP-UM-A-63-65408

Non Patent Literature

NPL 1: P. B. Roemer, W. A. Edelstein, C. E. Hayes, S. P. Souza, and O. M. Mueller: "The NMR Phased Array", Magnetic Resonance in Medicine, vol. 16, pp. 192-225 (1990).

SUMMARY OF INVENTION

Problems that the Invention is to Solve

However, in a deformable RF coil used as a lower coil that forms a pair with respect to an upper coil, such as an RF coil permanently mounted on a top plate or an RF coil built in the top plate, characteristics of the coil are changed between a case where the coil is used in a closely wound state with respect to a subject and a case where the coil is used without being wound. Thus, when the RF coil is a reception coil, an SN ratio is reduced, and when the RF coil is a transmitting coil, power necessary for an RF power amplifier is increased, or an SAR is increased.

Further, in both the RF coil dedicated to each portion and the wide range RF coil, in the case of a flexible coil used by deforming a coil shape according to the shape of an imaging object or the size of a subject, characteristics of the coil are changed according to its shape change. Thus, when the RF coil is a reception coil, the SN ratio is reduced, and when the RF coil is a transmitting coil, power necessary for an RF power amplifier is increased, or the SAR is increased.

Accordingly, an object of the invention is to provide an RF coil which is at least partially deformable according to a subject and constantly realizes a high SN ratio or high emission efficiency regardless of its shape. Further, another object of the invention is to provide a flexible RF coil dedicated to each portion used by similarly deforming a coil shape according to the shape or size of an imaging object, capable of constantly realizing a high SN ratio or high emission efficiency regardless of the shape.

Means for Solving the Problems

In order to solve the above problems, in an RF coil which is at least partially deformable according to a subject, at least one correction circuit for correcting a matching state and a tuned state of the coil that vary according to its shape is provided, and the correction circuit is switched by an output of a unit that detects the coil shape. Further, in a flexible RF coil dedicated to each portion used by similarly deforming the coil shape according to the shape of an imaging object or the size of a subject, at least one correction circuit for correcting the matching state and the tuned state of the coil that vary according to the shape is provided, and the correction circuit is switched by the output of the unit that detects the coil shape.

As the unit that detects the coil shape, a patient fixture (for example, a fixing belt) used when closely fixing the coil to a subject is used. For example, the patient fixture may have a structure in which plural connectors and plural lines are provided in a flexible material, a connector provided in the fixture and a connector provided in the coil are connected to each other, so that the subject is fixed together with the flexible coil deformed into a shape depending on the shape of the subject. By arranging a fixture-side connector and a coil-side connector so that the coil shape and a combination of the connected connectors correspond to each other respectively, the coil shape is recognized by the combination of the connected connectors.

A correction circuit necessary according to the coil shape is controlled to enter an electrically operated state by the above-described method. As the correction circuit, a circuit that controls a matching circuit according to a load of a transmitting coil, disclosed in PTL 4 is used, or a switch circuit and at least a part of a matching circuit or a tuning circuit, disclosed in PTL 5, is used.

Advantage of the Invention

According to the invention, with respect to an RF coil which is deformable according to a subject, it is possible to realize a coil which does not deteriorate in performance due to deformation of the coil. Particularly, in the case of a reception coil, it is possible to constantly realize a high SN ratio regardless of the shapes of the coil and the subject. Further, when the RF coil is also used as a transmitting coil, it is possible to constantly maintain a matching state regardless of the shapes of the coil and the subject, and to realize high emission efficiency with a low SAR. Furthermore, if a transmission/reception switch for switching emission and reception is provided, it is possible to realize a transmission/reception coil with a low SAR, while constantly securing high emission efficiency and a high SN ratio regardless of the shapes of the coil and the subject.

In addition, if the technique of the invention is applied to a patient fixture used when performing imaging while moving a posture or a joint of a subject using a joint motion device or the like, it is possible to provide a flexible RF coil according to each portion with constantly excellent performance and a device thereof with low cost.

BRIEF DESCRIPTION OF DRAWINGS

FIG. 15 is a diagram illustrating an example of a connector used in the second embodiment, in which FIG. 15(a) shows an RF coil-side connector, FIG. 15(b) shows a fixture-side connector, FIG. 15(c) is a circuit diagram when the RF coil-side connector and the fixture-side connector are separated from each other, and FIG. 15(d) is a circuit diagram when the RF coil-side connector and the fixture-side connector are fitted to each other.

DESCRIPTION OF EMBODIMENTS

Figure 1:
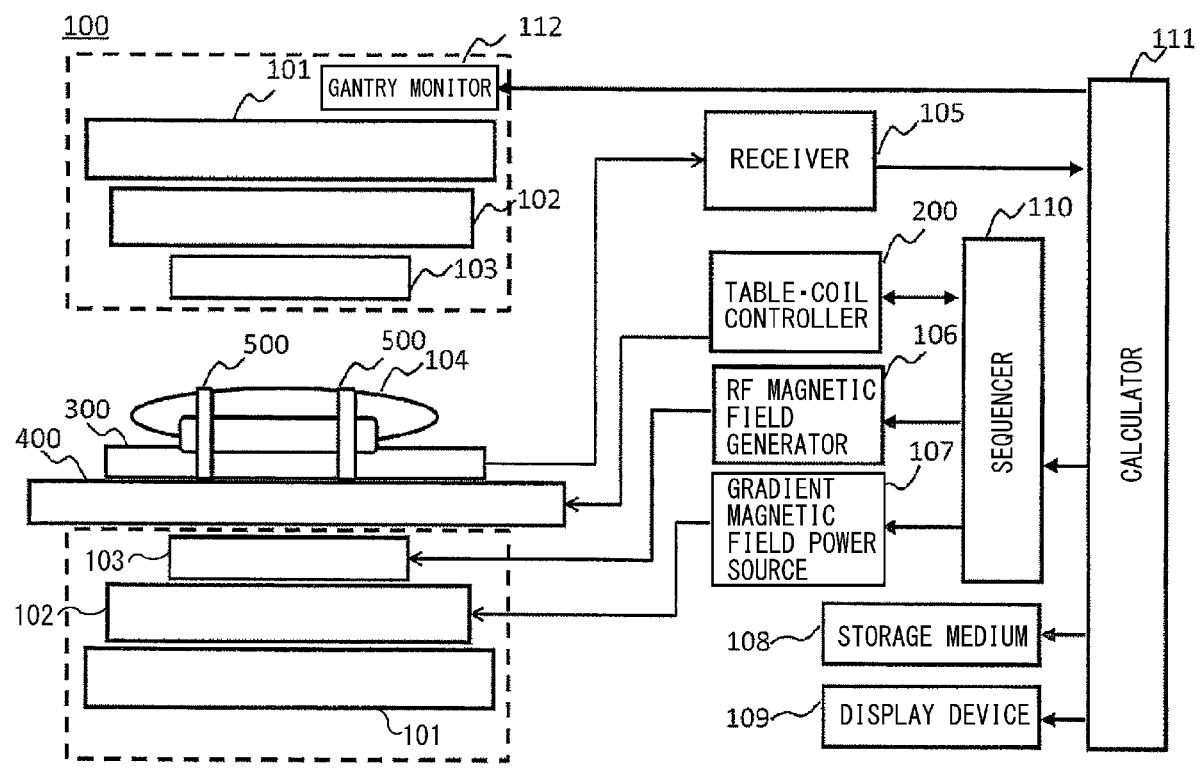
FIG. 1 is a block diagram illustrating a configuration of an MRI apparatus according to a first embodiment of the invention.
Figure 2:
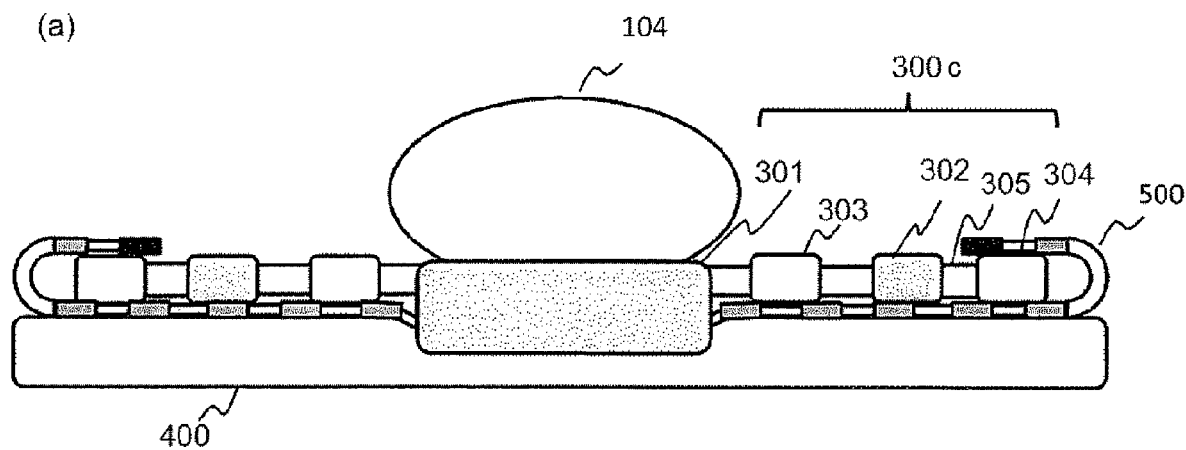
FIG. 2(a) is a sectional view of an RF coil permanently mounted on a top plate and a fixture in the embodiment.
FIG. 2(b) is a plan view thereof.
Figure 2:
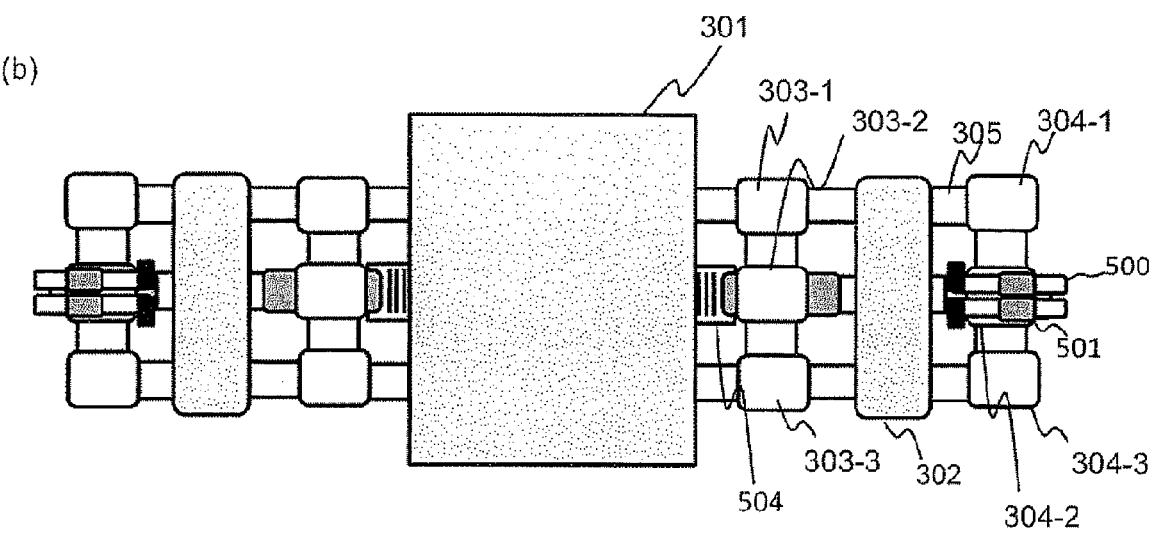

Hereinafter, embodiments of the invention will be described with reference to FIGS. 1 to 20. In the following description, the same reference numerals are given to the same components having the same functions and configurations, and description thereof will not be repeated.

First Embodiment

First, an MRI apparatus according to a first embodiment of the invention will be described with reference to FIGS. 1 to 10.

The MRI apparatus of the first embodiment includes a gantry 100 provided with a static magnetic field generator (101) that generates a static magnetic field and a gradient magnetic field generation coil 102 that generates a gradient magnetic field, a table 400 that is disposed in the gantry 100 for mounting a test object 104 thereon, and an RF coil 300 that receives a nuclear magnetic resonance signal generated from the test object 104 (FIG. 1). The RF coil 300 is configured so that a part (301) thereof is fixed to the gantry 100 or the table 400 and at least another part (300c) thereof is formed of a flexible material and is deformable to be in contact with the test object 104 (FIGS. 2(a) and 2(b), and FIG. 3). Further, the MRI apparatus includes a fixture 500 for fixing the RF coil 300 around the test object 104, a detector (306 and 505) that detects the shape of the RF coil 300, and a matching switch circuit 307-2 and a tuning switch circuit 307-1 that change the matching constant and the tuning constant of the RF coil 300 according to an output of the detector (306 and 505) (FIG. 2 and FIGS. 4 to 6).

For example, when the test object 104 is placed on the RF coil 300 in a state where the RF coil 300 is flatly mounted on the table 400, the RF coil 300 includes matching circuits (309-1 and 309-2) and tuning circuits (308-1 to 308-5) configured to be in an optimal matching state and an optimal tuned state. The detector (306 and 505) includes an RF coil-side connector 306 provided to be ancillary to the RF coil 300, a fixture-side connector 505 provided to be ancillary to the fixture 500, and mechanism switches (307-1a, 307-1b, and 307-2a) that turn on or off connection between terminals when the RF coil-side connector 306 and the fixture-side connector 505 are connected to each other. The matching switch circuit 307-2 and the tuning switch circuit 307-1 have a circuit configuration that varies according to turning on or off of the mechanism switches (307-1a, 307-1b, and 307-2a), and respectively switch the matching circuits 309-1 and 309-2 and the tuning circuits 308-1 to 308-5 into an optimal matching state and an optimal tuned state in the shape of the RF coil 300 corresponding to each of an on state and an off state of the mechanism switches (307-1a, 307-1b, and 307-2a).

Figure 7:
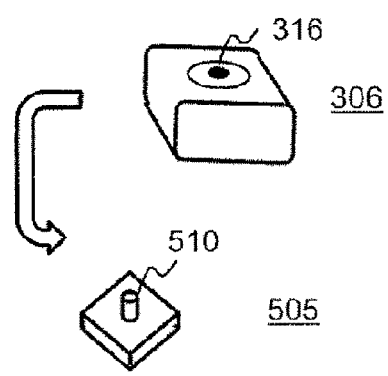
FIG. 7 is a diagram illustrating an example of a connector used in the first embodiment.

Further, for example, the mechanism switches (316, 510, 307-1a, 307-1b, and 307-2) are configured to include a switching button (316) pressed when the RF coil-side connector 306 is fitted to any one of the plural fixture-side connectors 505, and the switches (307-1a, 307-1b, and 307-2a) that turn on or off the connection between the terminals by the switching button (FIG. 7).

Hereinafter, this embodiment will be described more specifically. FIG. 1 is a diagram illustrating a configuration of an MRI apparatus of this embodiment. The gantry 100 includes the magnet 101 that generates a static magnetic field, the gradient magnetic field generation coil 102 that generates a gradient magnetic field, and a radio frequency transmitting coil 103 that generates a radio frequency magnetic field. In the gantry 100, the RF coil 300 is provided on a top plate of the patient table 400, and the subject (test object) 104 is placed thereon. Further, positions of the RF coil 300 and the subject 104 are fixed by the fixture 500. Generally, the gradient magnetic field generation coil 102 is configured by tri-axial gradient magnetic field coils that are orthogonal to each other. Further, a sequencer 110 transmits a command to a gradient magnetic field power source 107 and a radio frequency magnetic field generator 106, and generates a gradient magnetic field and an RF pulse from the gradient magnetic field coil 102 and the radio frequency transmitting coil 103, respectively. Normally, the radio frequency magnetic field generator 106 is configured by an RF pulse generator and a power amplifier that amplifies an RF pulse. An amplified RF pulse output is applied to the subject 104 through the radio frequency transmitting coil 103 at a timing depending on the command from the sequencer 110. Further, the gradient magnetic field power source 107 applies a gradient magnetic field to the subject 104 from each of the tri-axial gradient magnetic field coils at a timing depending on a command from the sequencer 110. A magnetic resonance signal generated from the subject 104 is received by the RF coil 300, is amplified by a pre-amplifier (not shown) in the RF coil, and then, is transmitted to a receiver 105. In the receiver 105, the signal is subjected to appropriate signal processing, is A/D converted (sampled), and then, is detected. The detected signal is transmitted to a calculator 111, is subjected to re-sampling, and then, is subjected to digital signal processing such as image reconstruction. Then, the result is displayed in a display device 109. Further, digital data or measurement conditions may be stored in a storage medium 108 as necessary. The sequencer 110 performs a control so that each device is operated at a timing and an intensity that are programmed according to the measurement conditions stored in the storage medium 108 or a command received from the calculator 111. A program in which timings of application of an RF pulse, application of a gradient magnetic pulse, and reception of a nuclear magnetic resonance signal or intensities of the RF pulse and the gradient magnetic field are written, among the programs, is particularly referred to as an imaging sequence.

Hereinafter, configuration conditions for realizing this embodiment will be described with reference to FIGS. 2 to 6.

Figure 3:
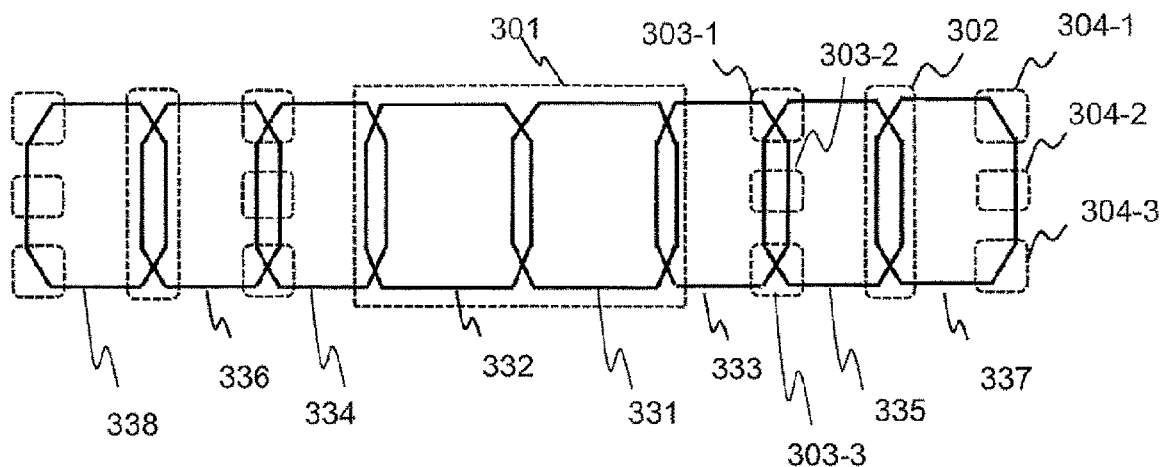
FIG. 3 is a plan view illustrating patterns of coil elements of the RF coil permanently mounted on the top plate.
Figure 4:
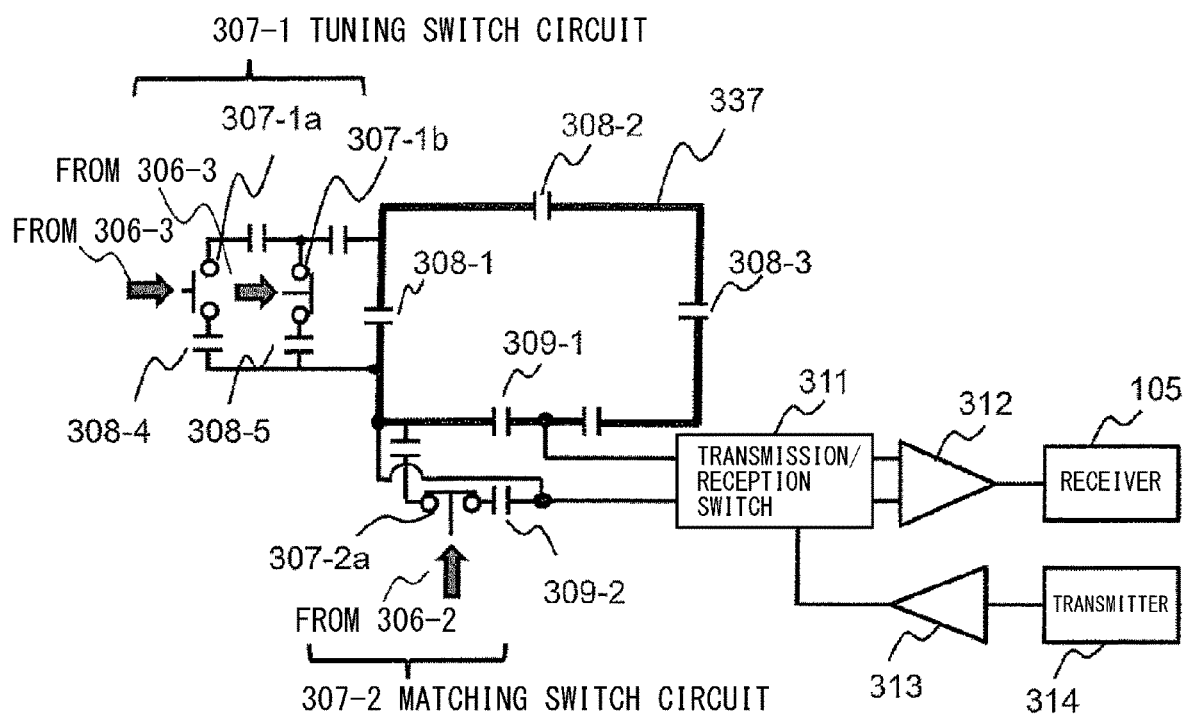
FIG. 4 is a circuit diagram illustrating details of the coil elements of the RF coil.

FIG. 2(a) is a sectional view of the patient table 400, the RF coil 300 and the fixture 500 that are constantly provided or built in the patient table 400, and FIG. 2(b) is a top view thereof. FIG. 3 is a plan view illustrating patterns of coil elements provided in the RF coil 300. In FIG. 3, a detailed circuit of the coil elements is not shown. As shown in FIG. 3, approximately rectangular loop-shaped coil elements 331, 332, 333, 334, 335, 336, 337, and 338 are arranged so that adjacent coil elements are partially overlapped. Portions of the adjacent coil elements that overlap each other are crossed in a bridge form so as not to be electrically conducted. In the resin case 301 made of a hard resin material, patterns of the entirety of the central coil elements 331 and 332, and a part of the coil elements 333 and 334 are formed. In a resin case 302, patterns of overlapping portions of the coil element 335 and the coil element 337 are formed. In resin cases 303-1 and 303-3, patterns of crossing portions of the coil element 333 and the coil element 335 are formed. In a resin case 303-2, longitudinal pattern portions of the coil element 333 and the coil element 335 that overlap each other are formed. The coil element 337 is disposed at the right end, and thus, does not have a structure in which an end portion thereof overlaps a different coil element, but an inclined pattern portion of the coil element 337 is covered with resin cases 304-1 and 304-3. Further, a central portion of a longitudinal pattern thereof is also covered with a resin case 304-2. Portions other than the portions covered with the resin cases 301, 302, 303-1 to 303-3, and 304-1 to 304-3, of the respective coil elements, are covered with a resin made of a flexible material. The RF coil 300 is provided, in addition to the coil elements 331 to 338 arranged as described above, with the tuning switch circuit 307-1 and the matching switch circuit 307-2 for the coil, which belong to the coil elements (FIG. 4). The tuning switch circuit 307-1 and the matching switch circuit 307-2 are provided in the resin cases 301, 302, 303-1, 303-2, 302-3, 304-1, 304-2, 304-3, and the like. Further, a power source circuit and a matching circuit of a coil are also provided in the resin case 301. The power source circuit includes a pre-amplifier power source used in reception. Further, when the RF coil 300 is a reception coil, the power source circuit also includes a detuning circuit power source for preventing coupling with a transmitting coil. The power source circuit is provided in the resin case 301, but if the RF coil 300 is constantly provided or built into the patient table, the power source circuit may also be provided in the patient table.

FIG. 4 is a circuit diagram illustrating details of the coil element 337 among the coil elements 331 to 338 shown in FIG. 3 and circuits which are ancillary thereto. The capacitors 308-1 to 308-5 form a coil tuning circuit. The capacitors 309-1 and 309-2 form a matching circuit. Since FIG. 4 shows a case where the RF coil is a transmission/reception coil, a detuning circuit necessary for a reception coil is not provided. The reception coil is configured by an inductor and a diode so that a detuning circuit performs parallel resonance with respect to a tuning capacitor. Further, reference numeral 311 represents a transmission/reception switch for switching transmission or reception, reference numeral 312 represents a reception low noise amplifier, reference numeral 313 represents an emission power amplifier, reference numeral 314 represents a radio frequency waveform generator, and reference numeral 105 represents the receiver. The tuning switch circuit 307-1 includes the switch 307-1*a* which is normally in a non-conductive state and is in a conductive state when the plug 510 of the connector 505 (which will be described later) is fitted to the catcher 316, and the switch 307-1*b* which is normally in a conductive state and is in a non-conductive state when the plug 510 of the connector 505 is fitted thereto. The matching switch circuit 307-2 includes the switch 307-2*a* which is normally in a conductive state and is in a non-conductive state when the plug 510 of the connector 505 is fitted to the catcher 316.

Figure 5:
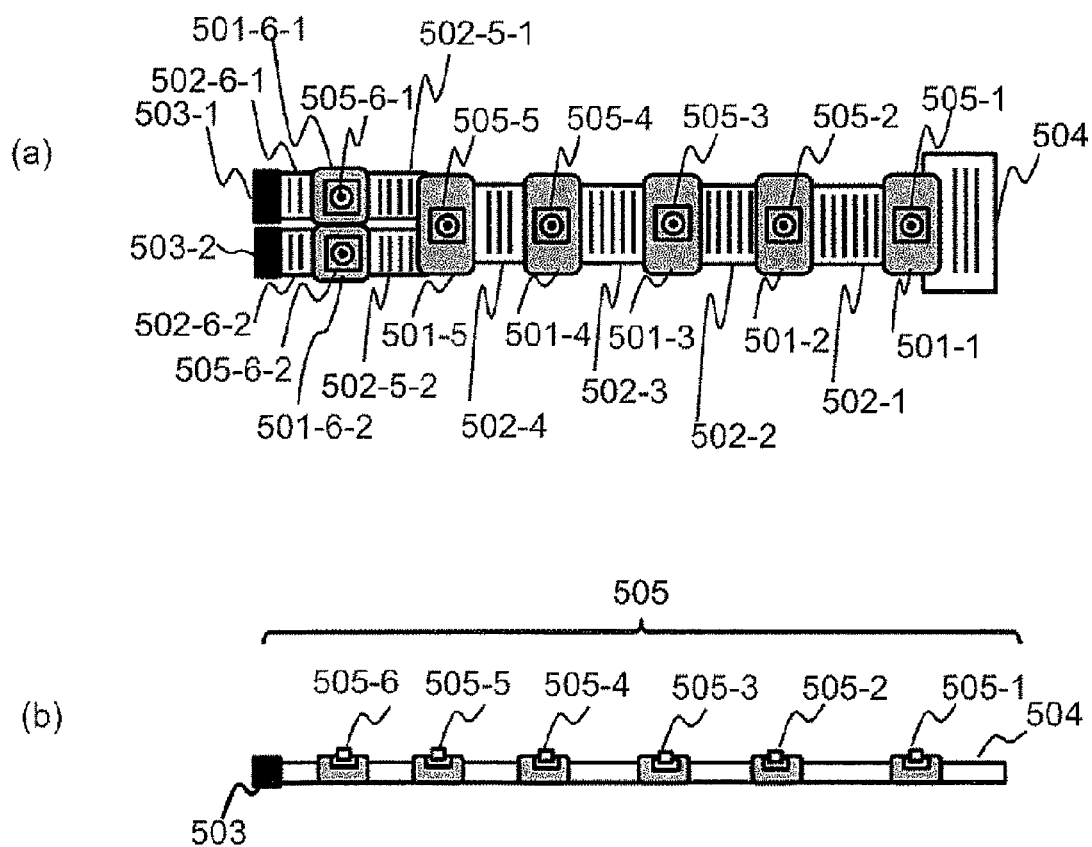
FIG. 5(a) is a plan view of the fixture used in the RF coil.
FIG. 5(b) is a sectional view thereof.

FIG. 5 shows the fixture 500 used when the RF coil 300 is fixed together with the subject 104, in which FIG. 5(*a*) is a plan view illustrating a state where the fixture 500 is two-dimensionally opened, and FIG. 5(*b*) is a sectional view illustrating the same state. The patient fixture 500 includes a flexible portion 504 of which an end is fixed to the patient table 400, and has a structure in which connector portions 501-1 to 501-6 and flexible portions 502-1 to 502-6 are connected to each other. Further, connecting portions 503-1 and 503-2 are respectively connected to flexible portions 502-6-1 and 502-6-2. The fixture 500 is configured to be bent in the flexible portions 502-1 to 502-6 and 504, and thus, may be wound around the RF coil 300. At central positions of upper surfaces of the connector portions 501-1 to 501-6-2, fixture-side connectors 505-1 to 505-6-2 are respectively provided. The flexible portions 502-1 to 502-6 are formed of a flexible material, and thus, the fixture 500 may be bent to be wound around the RF coil 300. Further, the connector 501-5 branches out into flexible portions 502-5-1 and 502-5-2 in a leftward direction.

Figure 6:
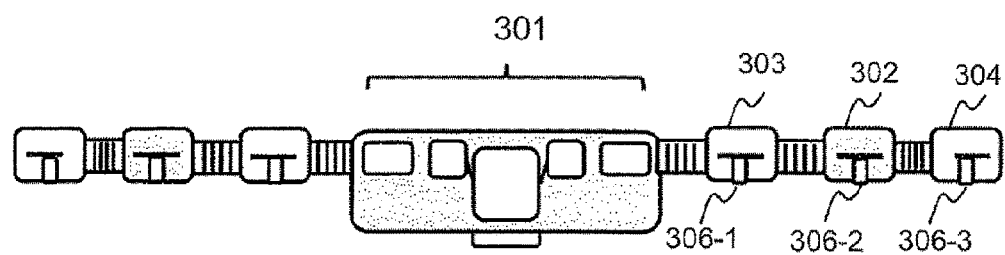
FIG. 6(a) is a sectional view of a connector position of the RF coil.
FIG. 6(b) is a plan (bottom) view of the RF coil.
Figure 6:
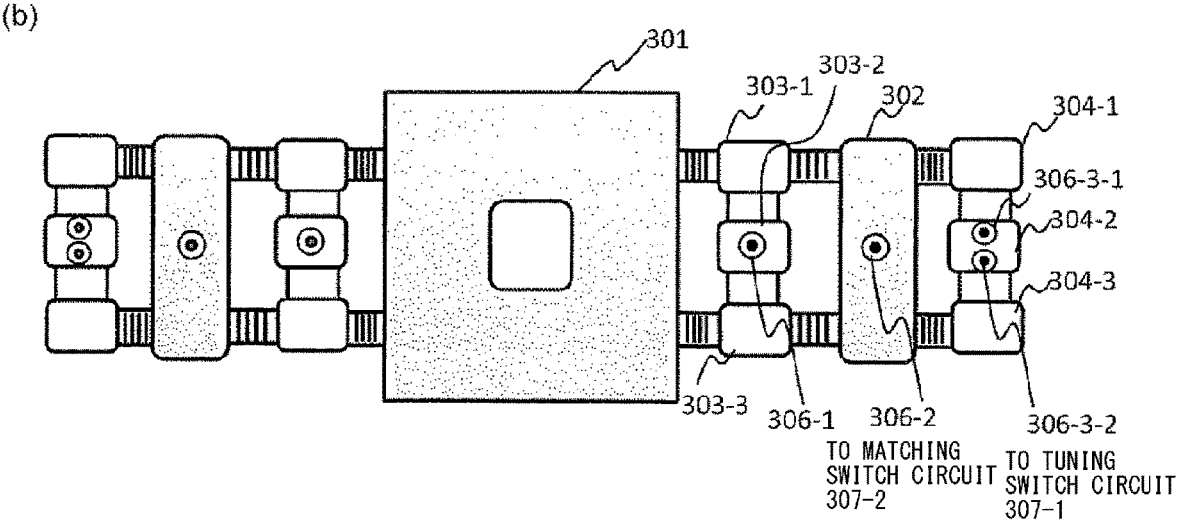

FIG. 6(*a*) is a sectional view illustrating a section passing through the center of the connector of each resin case of the RF coil 300, and FIG. 6(*b*) is a bottom view of the RF coil 300. As shown in FIG. 6, in the RF coil 300, RF coil-side connectors 306-2, 306-1, and 306-3 are respectively provided on bottom sides of the cases 302, 303, and 304.

Structures of the respective connectors 505 and 306 are shown in FIG. 7. The fixture-side connector 505 is provided with the protrusion-shaped plug 510. The RF coil-side connector 306 is provided with the catcher 316. The plug 510 is fitted to the catcher 316 by being press-fitted into the catcher 316. Then, the connector 306 and the connector 505 are fixed to each other, and a switching button provided at the center of the catcher 316 is pressed by the plug 510. The switching button is interlocked with the switches 307-1*b* and 307-2*a* which are constantly in an on state and are in an off state only when the button is pressed, and the switch 307-1*a* which is constantly in an off state and is in an on state only when the button is pressed, and an output signal indicating whether or not the connectors are connected to each other is obtained by the switches.

Figure 8:
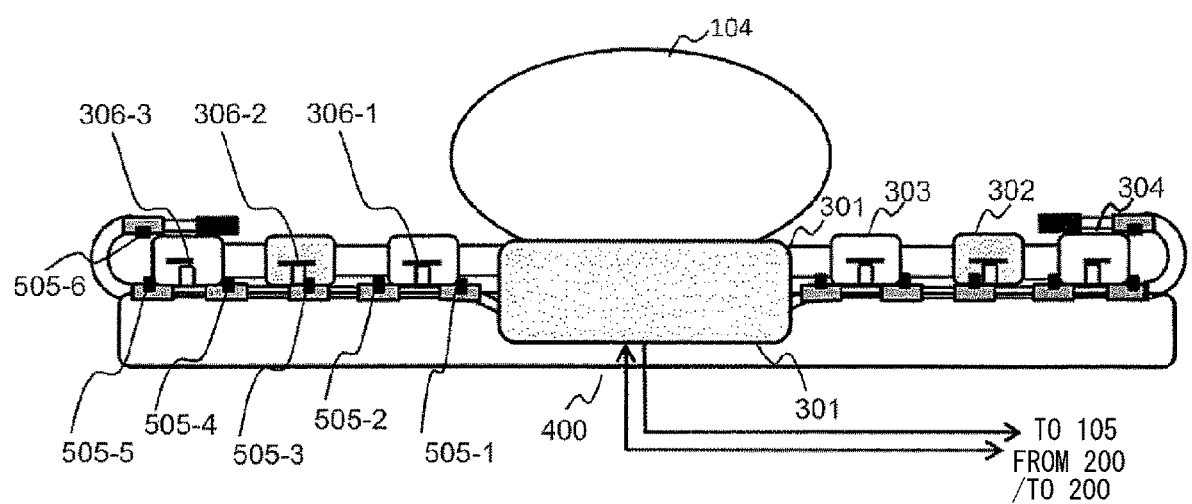
FIG. 8 is a sectional view of the RF coil used as a lower coil in a flat state.
Figure 9:
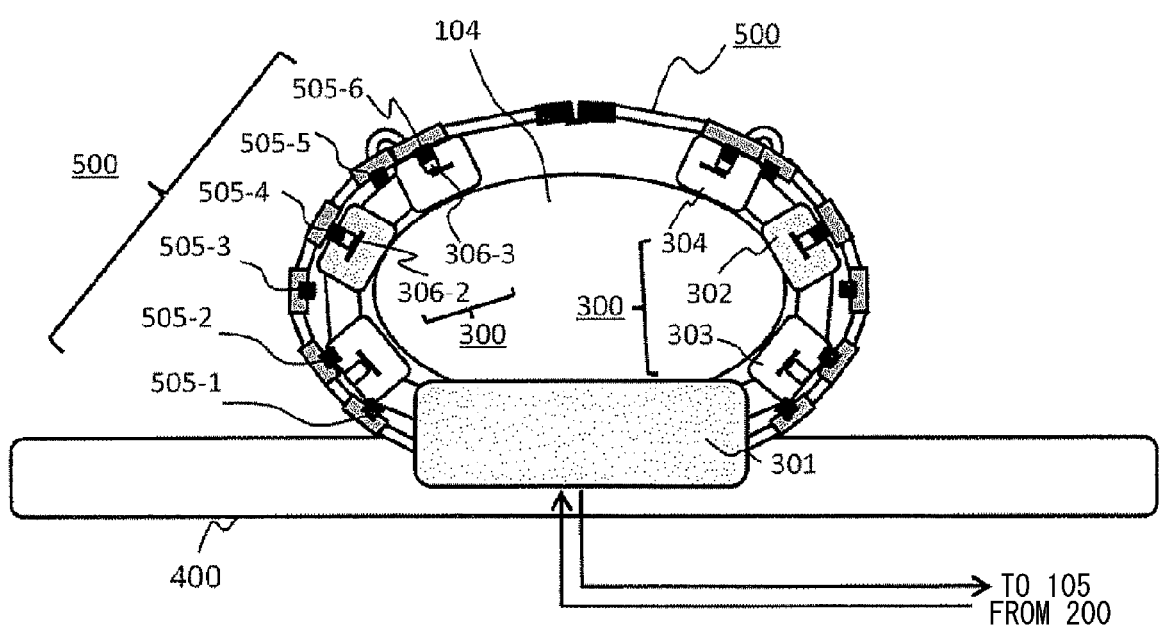
FIG. 9 is a sectional view of the RF coil used in a state of being wound around a subject.

FIG. 8 is a diagram illustrating a state where the flexible RF coil 300 of this embodiment is placed and used on the patient table in a flat state. The flat shape shown in FIG. 8 is frequently used when the RF coil 300 is used as a lower coil that forms a pair with respect to an upper coil (not shown in the figure) provided above a subject, compared with a case where the RF coil 300 is independently used as a reception coil or a transmission/reception coil. In this case, the respective connectors 306-1 to 306-3 and 505-1 to 505-5 are all in a non-connection state, and the switch 307-1*a* shown in FIG. 4 is in a non-conductive state (off), and the switches 307-1*b* and 307-2*a* are in a conductive state (on). Capacitance values of the capacitors 308-1 to 308-3, 308-5, 309-1 and 309-2 are selected so that the matching circuit and the tuning circuit of each coil element obtain optimal performance characteristics in these states. Next, FIG. 9 shows a state where the flexible RF coil 300 is used in a state of being wound around the subject 104. In this case, the RF coil-side connector 306-2 and the fixture-side connector 505-4 are connected to each other, and the RF coil-side connector 306-3 and the fixture-side connector 505-6 are connected to each other, in a state of being wound. If the connectors 306-2 and 505-4 are in a connection state, the plug 510 of the connector 505-4 is fitted to the catcher of the connector 306-2, and thus, the switch 307-2*a* shown in FIG. 4 is changed from the conductive state into the non-conductive state. That is, the matching circuit is switched from a state of being configured by the capacitors 309-1 and 309-2 into a state of being configured only by the capacitor 309-1. If the connectors 306-3 and 505-6 are in a connection state, the plug 510 of the connector 505-6 is fitted to the catcher 316 of the connector 306-2, and thus, the switch 307-1*a* shown in FIG. 4 is changed from the non-conductive state into the conductive state, and the switch 307-1*b* is changed from the conductive state into the non-conductive state. That is, a configuration in which the capacitor 308-5 is arranged in parallel to the capacitor 308-1 of the tuning circuit is switched into a configuration in which the capacitor 308-4 are arranged in parallel to the capacitor 308-1 of the tuning circuit.

As a specific example, an element (for example, 337) of the RF coil 300 which resonates at a frequency of 128 MHz, has a rectangular loop of which one side is about 15 cm in length, and is divided by three tuning capacitors 308-1 to 308-3 is considered, and a case where a cylindrical load equivalent to a subject having a waist size of about 30 cm in diameter is placed on the RF coil 300 is considered. When the flexible RF coil 300 is in a flat state, a distance between the element and the load is changed according to a channel.

According to an electromagnetic field simulation, it can be understood that an optimal value of the matching capacitor 309 of an element in which the distance from the load is short is about 48 pF, but an optimal value of the matching capacitor 309 of an element (337) in which the distance from the load is long is about 90 pF. On the other hand, when the load is placed on the flexible RF coil 300 in a wound state, it can be understood that the distance between the element and the load is approximately the same with respect to all channels and an optimal value of the matching capacitor 309 is about 35 pF. In any case, with respect to the capacitor 308 of the matching circuit, it can be understood that the optimal value is 10 pF±2 pF. Sensitivity in the flat state is high in a case where the matching capacitor 309 and the tuning capacitor 308 which are adjusted to be flat are used, compared with a case where the matching capacitor 309 and the tuning capacitor 308 which are adjusted to be in the wound state are used. On the other hand, it can be understood that sensitivity in the wound state has a small difference (about lower than 10%) between a case where the matching capacitor 309 and the tuning capacitor 308 which are adjusted in the flat state are used and a case where the matching capacitor and the tuning capacitor which are adjusted in the wound stated are used, at a central portion of the load, and that the sensitivity is high by 15% or more in a case where the matching capacitor 309 and the tuning capacitor 308 which are adjusted in the wound state are used, compared with a case where the matching capacitor 309 and the tuning capacitor 308 which are adjusted in the flat state are used, at a shallow portion from the surface of the load. That is, with respect to an element in which the distance from the load is long, if a capacitance value of the capacitor 309-1 is designed to be 35 pF and a capacitance value of the capacitor 309-2 is designed to be 55 pF, the synthetic capacity of the matching capacitor 309 is switched from 90 pF into 35 pF by a switch circuit. Further, if capacitance values of the tuning capacitors 308-1 to 308-3 are designed to be about 10 pF and capacitance values of the tuning capacitors 308-4 and 308-5 are designed to be about 6 pF, an optimal tuning capacitor can be selected by the switch circuit. As described above, it is possible to constantly realize an RF coil with high sensitivity either in the flat state or in the wound state. Hereinabove, an example in which the load equivalent to the subject 104 is a cylindrical shape is shown, but it can be understood that even when an elliptical load is used in FIG. 8, the same tendency is obtained and a difference between an optimal capacitance value in the flat case and an optimal capacitance value in the wound case is small compared with the cylindrical load.

Figure 10:
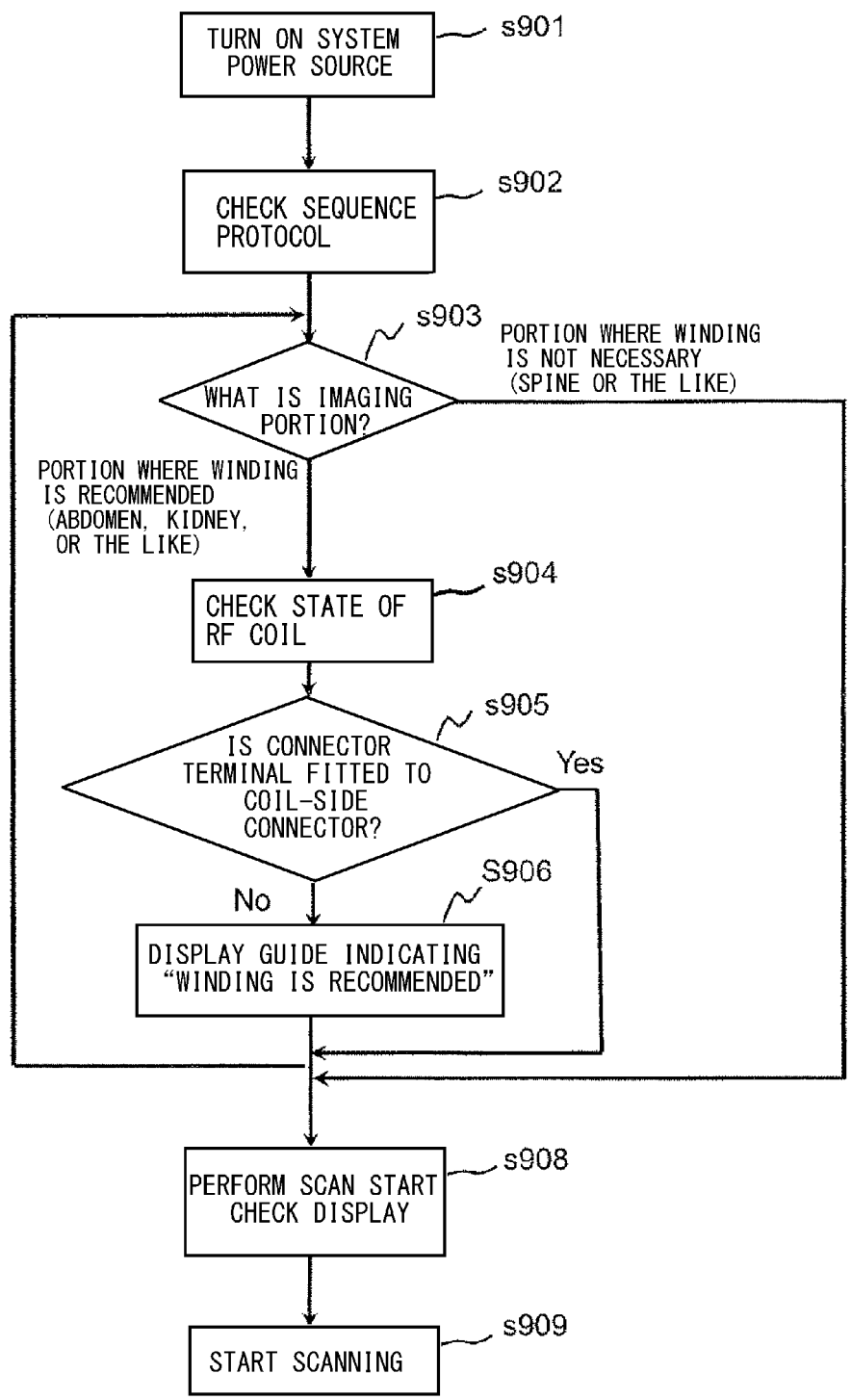
FIG. 10 is a flowchart illustrating a procedure of imaging starting according to the first embodiment of the invention.

FIG. 10 is a flowchart illustrating a procedure of imaging starting in an embodiment of the MRI apparatus in which the flexible RF coil is used. In this embodiment, the flexible RF coil 300 is permanently mounted on the patient table 400. If system power is supplied (s901), a sequence protocol is checked by the sequencer 100 for imaging preparation (s902). At the same time, power is also supplied to the patient table 400 and a power source (provided in the case 301) in the permanently mounted or built-in flexible RF coil 300 by a table coil controller 200. Then, it is determined what an imaging portion set in the sequencer 100 is (s903). When the determined imaging portion is a back side of the human body as in imaging of the spine, it is not necessary that the RF coil 300 is wound. Thus, the procedure proceeds to s908, and a scan starting confirmation display is performed as it is. On the other hand, when the determined imaging portion is a portion for which it is preferable that the coil is wound, such as the abdomen or the kidney of the human body, in order to check the state of the flexible RF coil 300 (whether the state is the flat state or the wound state), the state of the RF coil-side connector 306 is checked in s904. In s905, if the plug (terminal) 510 of the fixture-side connector 505 is fitted to any one of the RF coil-side connectors 306-1 to 306-3, that is, if any one of the connectors 306-1 to 306-3 is in a state of being connected to the fixture-side connector 505, it is determined that the RF coil 300 is in the wound state. Further, as shown in FIG. 9, if the plug (terminal) 510 of the connector 505 is fitted to the RF coil-side connectors 306-2 and 306-3, as described with reference to FIG. 4, values of the capacitors 308 and 309 of the matching circuit or the tuning circuit are automatically switched into values which are optimally adjusted in the wound state. Accordingly, the procedure proceeds to s908, and the scan starting confirmation display is performed. On the other hand, if the plug (terminal) 510 of the connector 505 is not fitted to any one of the RF coil-side connectors 306-1 to 306-3, that is, if the connectors 306-1 to 306-3 are in the non-connection state with respect to the fixture-side connector 505, the table coil controller 200 detects this state through a circuit in the coil. Then, the procedure proceeds to s906, and a screen for prompting the winding of the RF coil 300 based on a control method programmed by the sequencer 110 and the calculator 111 is displayed in the display device 109 or a gantry monitor 112. In order to detect whether or not the plug (terminal) 510 of the connector 505 is fitted to any one of the RF coil-side connectors 306-1 to 306-3 by the table coil controller 200, for example, switches that are turned on by fitting of the plug (terminal) 510 of the connector 505, similar to the switch 307-1a shown in FIG. 4, are respectively added to the coil-side connectors 306-1 to 306-3 shown in FIG. 6, and a signal line for transmitting a logical sum of outputs of the switches to the RF table coil controller 200 is provided in the RF coil.

After the above-described flow is finished, the scan starting confirmation display is performed in the display device 109 (s908), and the scanning is started (s909). After the scan is started, the sequencer 110 sends a command to the gradient magnetic field power source 107 and the radio frequency magnetic field generator 106, and generates a gradient magnetic field and an RF pulse from the gradient magnetic field coil 102 and the radio frequency transmitting coil 103, respectively. The radio frequency magnetic field generator 106 configured by the RF pulse generator 314 and the power amplifier 313 that amplifies an RF pulse causes the radio frequency transmitting coil 103 to emit an output of the RF pulse amplified at a timing depending on a command from the sequencer 110, and then, applies the result to the test object 104. Further, the gradient magnetic field power source 107 also applies a gradient magnetic field to the test object 104 from each of the tri-axial gradient magnetic field coils at a timing depending on a command from the sequencer 110. A magnetic resonance signal generated from the test object 104 is received by the flexible RF coil 300 of this embodiment, is amplified by a pre-amplifier (not shown in the figure) in the RF coil 300, and then, is transmitted to the receiver 105. In the receiver 105, the signal is subjected to appropriate signal processing, is A/D converted (sampled), and then, is detected. The detected signal is transmitted to the calculator 111, is subjected to re-sampling, and then, is subjected to digital signal processing such as image reconstruction. Then, the result is displayed in the display device 109.

As described above, in the first embodiment, when the flexible RF coil 300 is used in the flat state in terms of usability or is used in the wound state in terms of image quality according to imaging portions, optimal coil parameters (capacitor values of the matching circuit and the tuning circuit) are constantly selected. Thus, it is possible to realize a flexible RF reception coil having constantly high sensitivity, or a flexible RF transmission/reception coil having high emission efficiency.

In the above-described embodiment, a configuration in which the RF coil 300, the fixture 500, the detector (306 and 505), the matching switch circuit 307-2, and the tuning switch circuit 307-1 form a part of the MRI apparatus is described, but these components may be configured as an RF coil assembly to be independent from the MRI apparatus. In this case, the RF coil assembly may be connected to the conventional MRI apparatus for use.

Second Embodiment

Hereinafter, a second embodiment will be described with reference to FIGS. 11 to 18.

Figure 11:
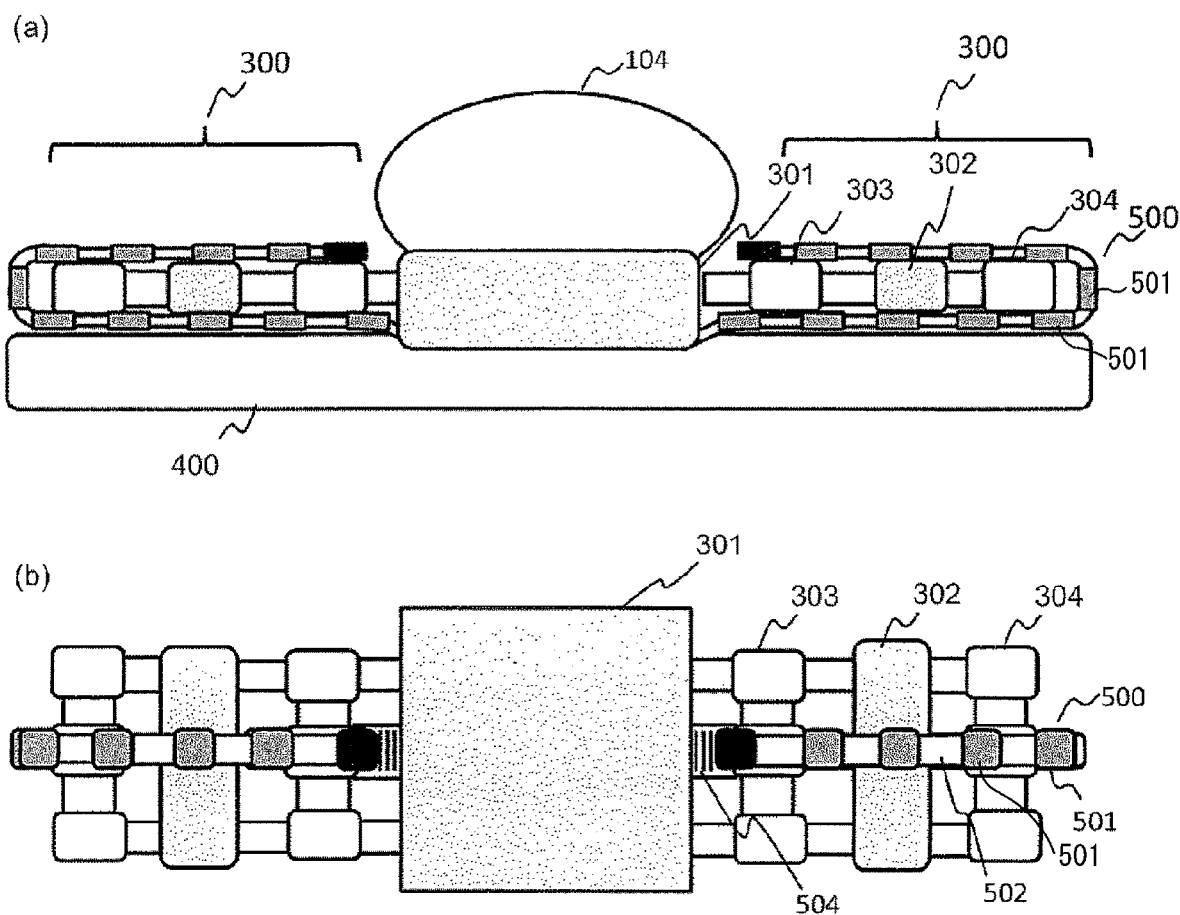
FIG. 11(a) is a sectional view of a fixture according to a second embodiment of the invention.
FIG. 11(b) is a plan view thereof.
Figure 12:
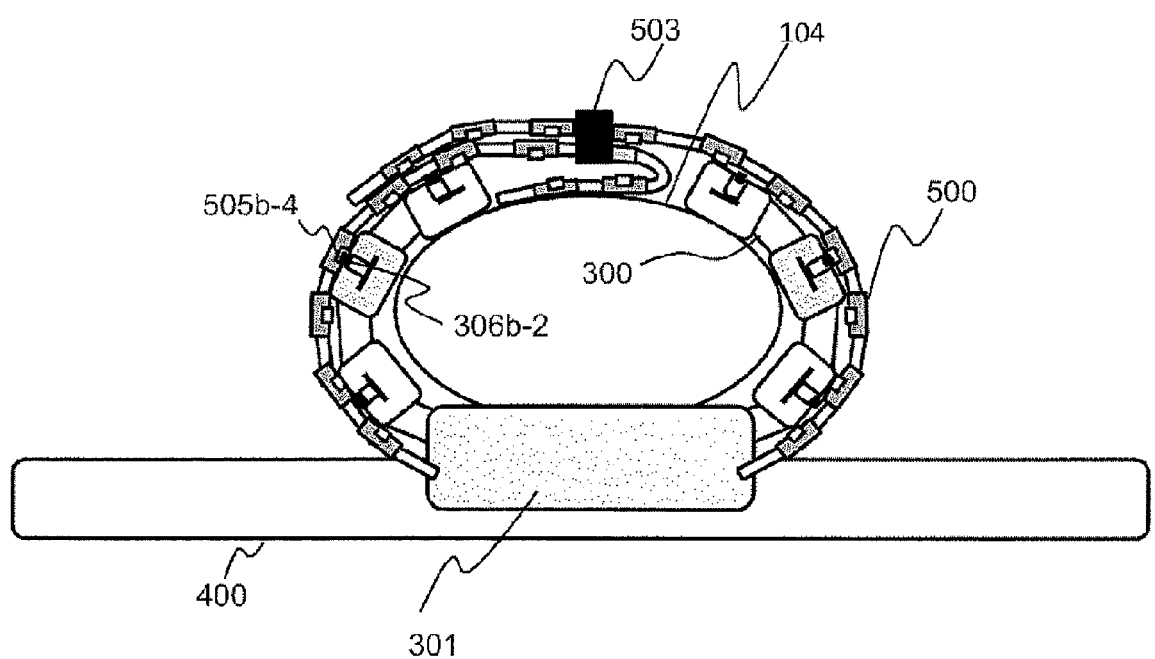
FIG. 12 is a sectional view illustrating a state where an RF coil of the second embodiment is wound around a subject.
Figure 15:
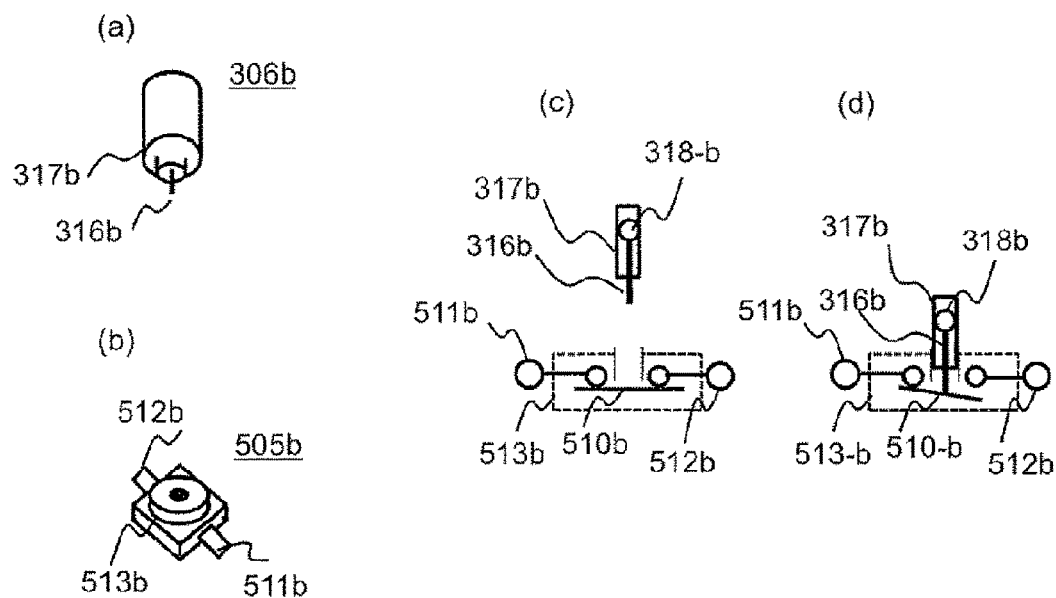
Figure 16:
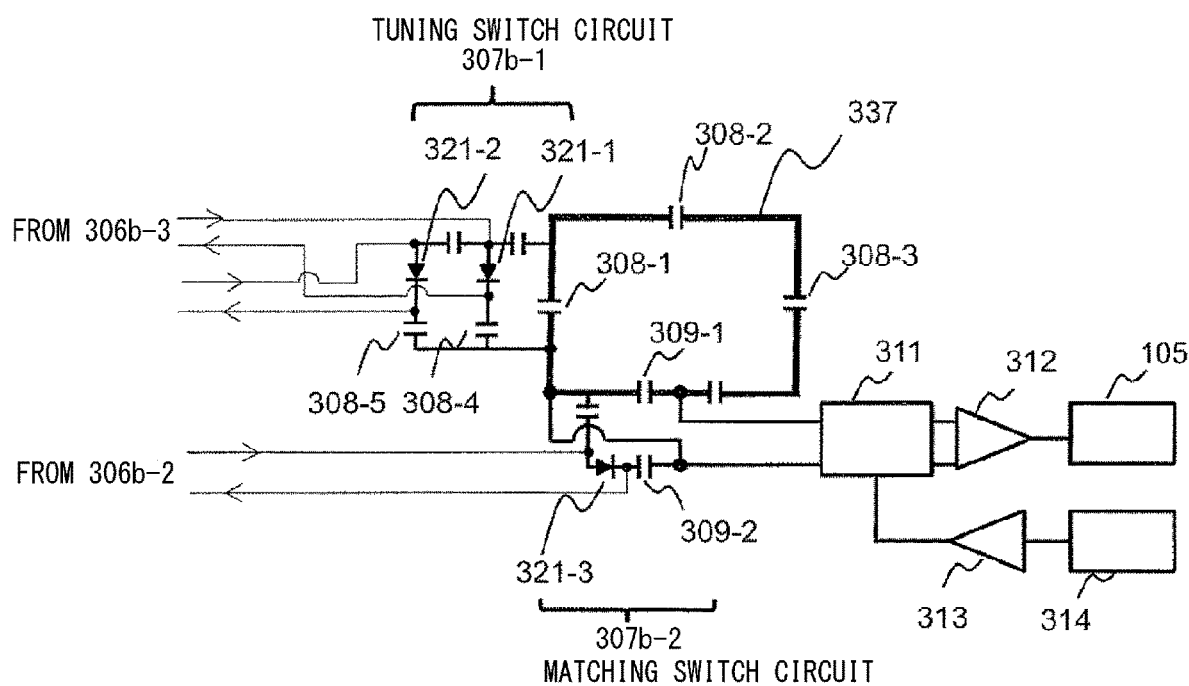
FIG. 16 is a circuit diagram illustrating details of coil elements of the RF coil of the second embodiment.

In the second embodiment, a detector (306b and 505b) includes an RF coil-side connector 306 provided to be ancillary to an RF coil 300, a fixture-side connector 505 provided to be ancillary to a fixture 500, and coaxial switch connectors (316b, 317b, and 513b) that transmit a control voltage supplied through an interconnection of the fixture 500 when the RF coil-side connector 306 and the fixture-side connector 505 are connected to each other (FIGS. 11, 12, and 15). A matching switch circuit 307b-2 and a tuning switch circuit 307b-1 have a circuit configuration that varies according to the control voltage transmitted from the coaxial switch connectors (316b, 317b, and 513b). Thus, matching circuits 309-1 and 309-2 and tuning circuits 308-1 to 308-5 are respectively switched into an optimal matching state and an optimal tuned state in a shape of the RF coil 300 corresponding to a connection state of the RF coil-side connector 306 and the fixture-side connector 505 (FIG. 16).

For example, the matching switch circuit 307b-2 and the tuning switch circuit 307b-1 may be respectively configured to include PIN diodes 321-1, 321-2, and 321-3 of which on and off states are changed by the control voltage transmitted from the coaxial switch connectors (316b, 317b, and 513b).

Figure 13:
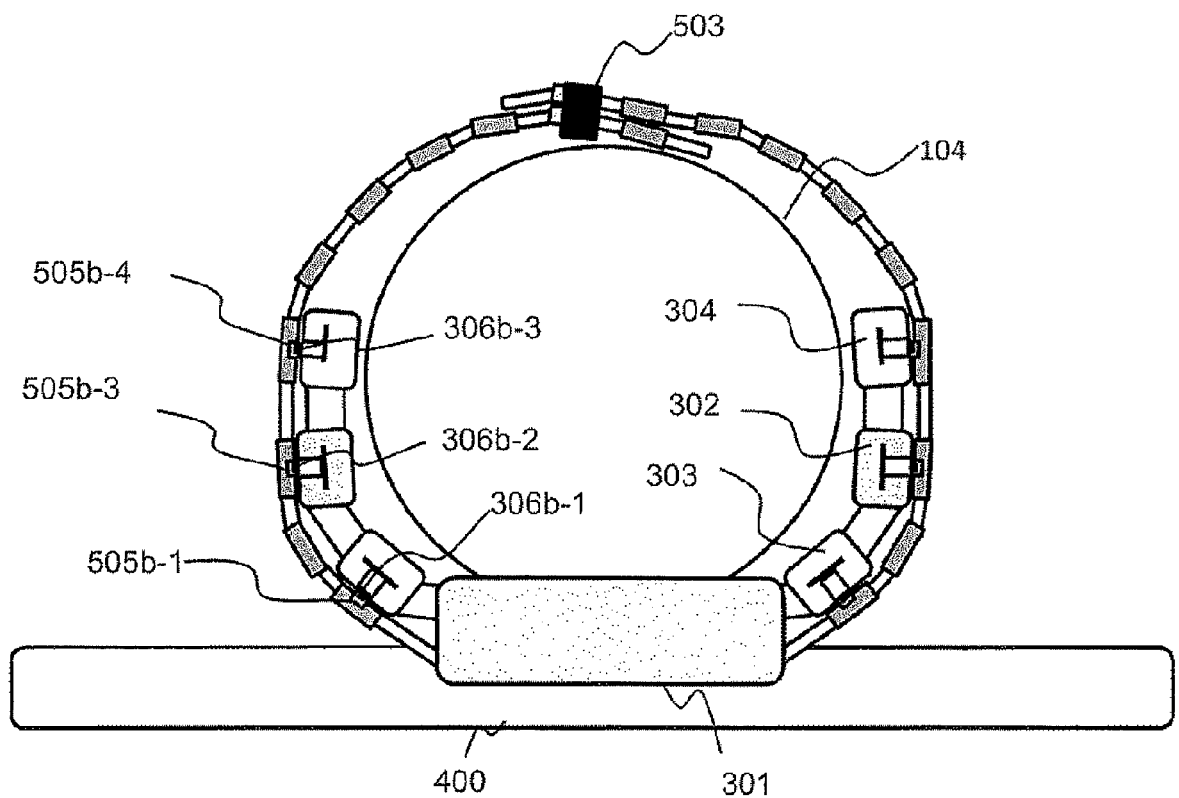
FIG. 13 is a sectional view illustrating a state where the RF coil of the second embodiment is used in imaging a large sized subject.
Figure 14:
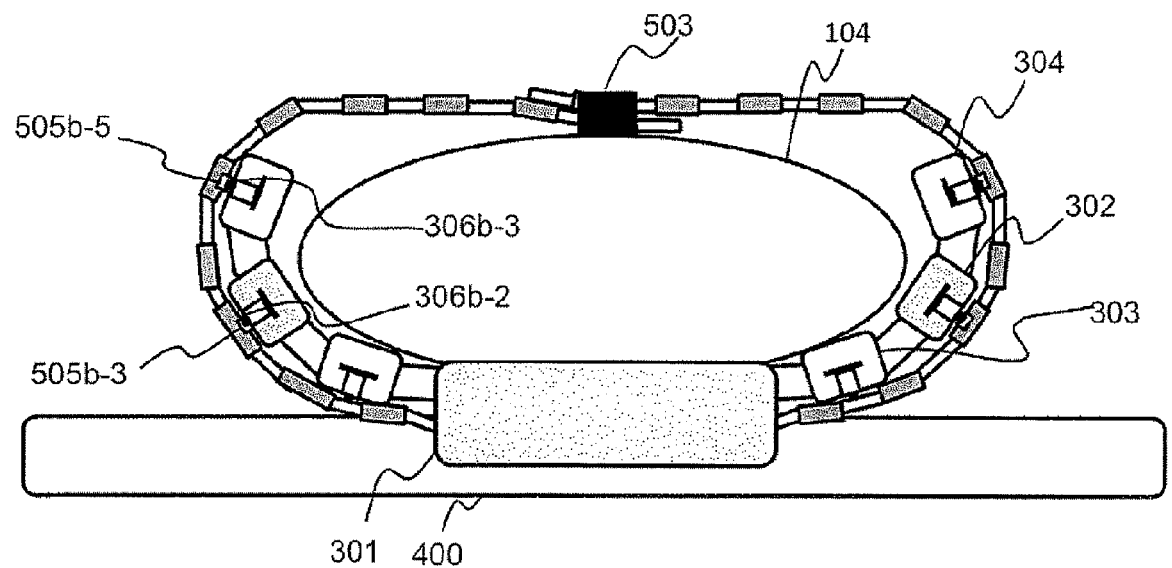
FIG. 14 is a sectional view illustrating a state where the RF coil of the second embodiment is used in imaging a small sized subject.

Hereinafter, this embodiment will be described more specifically. FIG. 11(a) is a sectional view illustrating a patient table 400 and the flexible RF coil 300 in the second embodiment, and FIG. 11(b) is a top view thereof. In the second embodiment, compared with the first embodiment, the numbers of connector portions 501 and flexible portions 502 of the fixture 500 are increased, and the entire length of the fixture 500 is increased. The fixture-side connector 505b is provided in the connector 501 of the fixture 500 similar to the first embodiment, but the second embodiment is different from the first embodiment in that the number of the connectors 501 is increased. FIGS. 12, 13, and 14 are sectional views illustrating a state where the flexible RF coil 300 of the second embodiment is wound around a subject 104. In the second embodiment, by increasing the length of the fixture 500, it is possible to wind the RF coil 300 around subjects of various sizes, and to increase the degree of freedom of a combination of the fixture-side connector 505b and the RF coil-side connector 306b to be connected to each other. For example, in the case of the subject 104 shown in FIG. 12, the combination of the connectors to be connected to each other corresponds to a configuration in which a fixture connector 505b-4 is connected to a coil-side connector 306b-2. Further, the length of the fixture 500 has a surplus, but in the surplus portion, electric connection is not necessary, and thus, the surplus portion may be fixed by an adjuster 503 or the like. Further, in the case of a subject shown in FIG. 13, a fixture-side connector 505b-1 is connected to a coil-side connector 306b-1, a fixture-side connector 505b-3 is connected to the coil-side connector 306b-2, and the fixture-side connector 505b-4 is connected to a coil-side connector 306b-3, respectively. In addition, in the case of a subject shown in FIG. 14, the fixture-side connector 505b-3 is connected to the coil-side connector 306b-2, and a fixture-side connector 505b-5 is connected to the coil-side connector 306b-3, respectively.

Further, as the coil-side connector 306b and the fixture-side connector 505b, the connectors shown in FIG. 7 may be used, but coaxial switch connectors 306b and 505b as shown in FIGS. 15(a) and 15(b) may be used. In the coaxial connectors shown in FIGS. 15(a) and 15(b), differently from the first embodiment, the RF coil-side connector 306b is formed in a plug shape, and the fixture-side connector 505b forms a catcher 513b that restricts the plug 316b. In the coaxial switch connectors, the plug 316b is mechanically fitted to the catcher 513b, and thus, an electric contact provided in the catcher 513b is turned on or off, and a tip of the plug 316b for fitting also becomes an electric contact. As shown in FIG. 15(a), the RF coil-side connector 306b includes a cylindrical chassis 317b and a central conductor (plug) 316b inside the cylindrical chassis 317b. The plug 316b is fitted to the catcher 513b of the fixture-side connector 505b shown in FIG. 15(b). Then, as shown in FIGS. 15(c) and 15(d), a spring conductor 510b inside the catcher 513b is pressed. Thus, connection between a first terminal 511b and a second terminal 512b, which is in a conductive state (on) as shown in FIG. 15(c) before fitting, is changed to a non-conductive state (off). Instead, as shown in FIG. 15(d), the tip of the central conductor 316b is in contact with the spring conductor 510b so that connection between the first terminal 511b and a third terminal 318b of the RF coil 300, which is connected to the central conductor (plug) 316b, is turned on. Further, the cylindrical chassis 317b is connected to a chassis 317b of the catcher 513b.

If the coaxial switch connectors 306b and 505b are used, as shown in FIG. 16, it is possible to use a circuit that performs an electric control using a semiconductor element 321 (in FIG. 16, a case where a PIN diode is used is shown as an example) as the matching switch circuit 307b-2 or the tuning switch circuit 307b-1.

Figure 17:
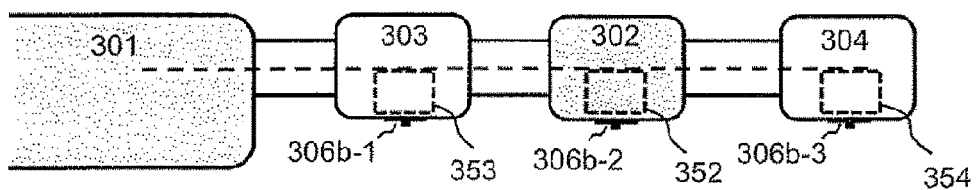
FIG. 17(a) is a sectional view illustrating the RF coil of the second embodiment.
FIG. 17(b) is a sectional view illustrating a structure of the fixture.
FIG. 17(c) is a circuit diagram illustrating connection of a multi-layer interconnection substrate in the fixture and coaxial switch connectors.
Figure 17:
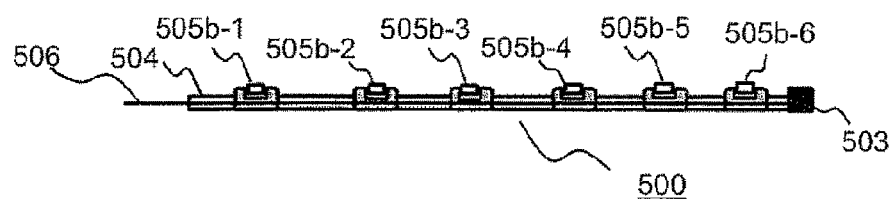
Figure 17:
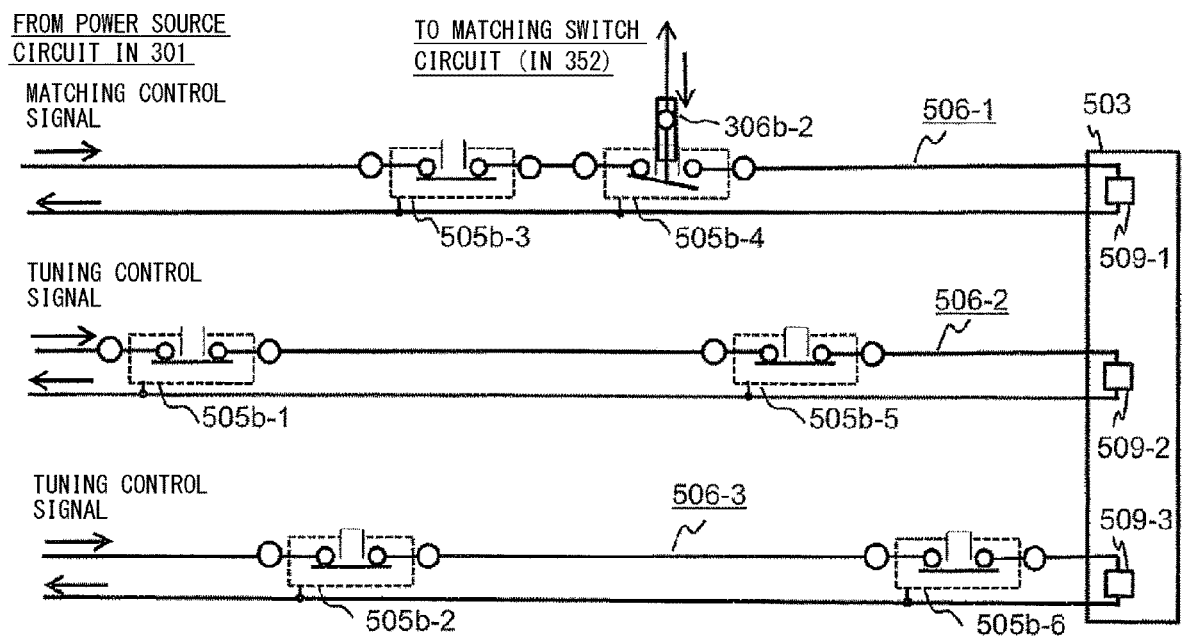
Figure 18:
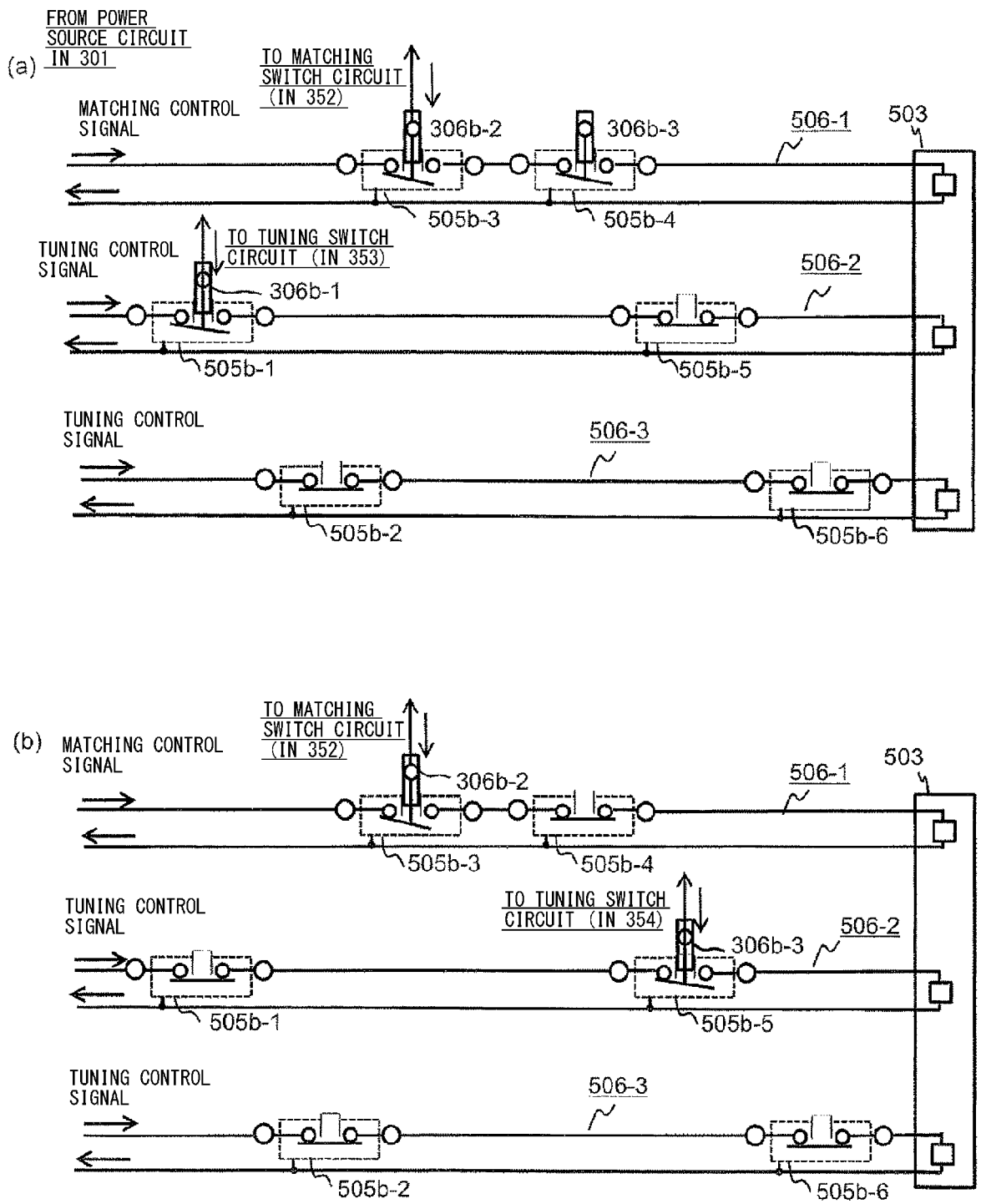
FIG. 18(a) is a circuit diagram illustrating connection in the fixture of the second embodiment corresponding to FIG. 13.
FIG. 18(b) is a circuit diagram illustrating connection in the fixture of the second embodiment corresponding to FIG. 14.

FIG. 17 shows a structure of the RF coil 300 of the second embodiment using the coaxial switch connectors 306b and 505b and a flexible interconnect substrate. FIG. 17(a) is an appearance view illustrating a part (right half) of the flexible RF coil 300. A resin case 301, and resin cases 303, 302 and 304 that are arranged in a rightward direction from the resin case 301 are sequentially connected through flexible portions. Coil elements 331, 333, 335, and 337 shown in FIG. 3 are formed in the resin cases. In FIG. 17(a), positions where the coil elements are formed are indicated by broken lines. Further, each of blocks 353, 352, and 354 inside the resin cases 303, 302, and 304 represents a tuning switch circuit or a matching switch circuit ancillary to each coil element. FIG. 17(b) shows a section of the fixture 500. One end of a flexible interconnect substrate 506 is fixed to the resin case 301. The flexible interconnect substrate 506 is sequentially connected to the connector 505b-1 to the connector 505b-6, and is finally connected to the fixture connecting portion 503.

Specifically, as shown in FIG. 17(c), three pairs of reciprocating (both way) lines 506-1 to 506-3 are formed on the flexible interconnect substrate 506. One end of each reciprocating line is connected to a power source inside the resin case 301. The other end thereof is connected to the fixture connecting portion 503, and is connected to each of dummy loads 509-1 to 509-3 in the connecting portion 503. Thus, a voltage of several volts is applied between a hot line and a GND line of each pair of reciprocating lines, so that a constant current flows therein. More specifically, inductors are disposed at uniform intervals on the way of the reciprocating lines to achieve high impedance in a radio frequency form, but are not shown in FIG. 17(c). In the example shown in FIG. 17(c), the connector 505b-1 which is on the root side of the fixture 500 is inserted into a second hot line 506-2, and then, the connector 505b-2 is inserted into a third hot line 506-3, the connector 505b-3 is inserted into a first hot line 506b-1, the connector 505b-4 is inserted into the first hot line 506-1, the connector 505b-5 is inserted into the second hot line 506-2, and the connector 505b-6 is inserted into the third hot line 506-2, respectively. The fixture 500 including the connectors 505b that are arranged in such an array form may be realized using a flexible interconnect substrate on which plural interconnections are formed in a single interconnect layer, or using a flexible interconnect substrate having a multi-layer interconnect layer.

If the RF coil-side connector 306b is inserted into any one of the fixture-side connectors 505b, as described with reference to FIG. 15, the coaxial paths are switched, and a voltage is applied to the matching switch circuit or the tuning switch circuit of the RF coil 300 through the inserted RF coil-side connector 306b. An example of a circuit of coil elements that include the matching switch circuit 307b-2 and the tuning switch circuit 307b-1 using such a configuration is shown in FIG. 16. That is, whether the capacitor 308-4 is added to the tuning capacitor 308-1 is determined by turning on or off of the PIN diode 321-3. In the example shown in FIG. 16, a forward control voltage is applied to the PIN diode 321-3 through the RF coil-side connector 306b-2 to turn on the PIN diode 321-3. Further, the PIN diode 321-1 is turned on by a control signal, and whether the capacitor 308-4 is additionally connected to the tuning capacitor 308-1 is determined by turning on or off of the PIN diode 321-1. This is controlled by whether the forward control voltage is applied to the PIN diode 321-1 through the RF coil-side connector 306b-3. Alternatively, whether the capacitor 308-5 is further added to the tuning capacitor 308-1 is controlled by turning on or off of the PIN diode 321-2. In the second embodiment, similarly, the mechanism switch shown in FIG. 7 may be used, but the position of the switch circuit 307 and the position of the RF coil-side connector 306 are restricted. Accordingly, in this embodiment, by employing the coaxial switch connectors shown in FIG. 15 to form an electric switch circuit, the restriction is alleviated, and thus, the degree of freedom in design is enhanced. Further, by increasing the parallel number of switch circuits, it is possible to relatively easily enlarge a variable width of capacitance values of the capacitors.

In the coil mounted state shown in FIG. 12, since the RF coil-side connector 306-2 and the fixture-side connector 505b-4 are connected to each other, as shown in FIG. 17(c), a control signal is transmitted to the PIN diode 321-3 for switching the tuning capacitor 309-1 shown in FIG. 16 from the connector 505b-4 connected to the first line 506-1 through the connector 306b-2. Further, in the coil mounted state shown in FIG. 13, the RF coil-side connector 306b-1 and the fixture-side connector 505b-1, the connector 306b-2 and the connector 505b-3, and the connector 306b-3 and the connector 505b-4 are connected to each other, respectively. Accordingly, as shown in FIG. 18(a), a control signal is transmitted to the PIN diode 321-1 for switching the tuning capacitor 308-1 through the connector 505b-1 connected to the second line 506-2 and the connector 306b-1. Further, a control signal is transmitted to the PIN diode 321-3 for switching the matching capacitor 309-1 through the connector 505b-3 connected to the first line 506-2 and the connector 306b-2. Here, with respect to the connection between the coaxial connector 306b-3 and the coaxial connector 505b-4, since the line is already switched in a former stage thereof, a control signal is not transmitted from the connector 306b-3 to the RF coil tuning circuit. Further, in the coil mounted state shown in FIG. 14, the connector 306b-2 and the connector 505b-3, and the connector 306b-3 and the connector 505b-5 are connected to each other, respectively. Accordingly, as shown in FIG. 18(b), a control signal is transmitted to the PIN diode 321-3 for switching the matching capacitor 309-1 from the first line 506-1 through the connector 505b-3 and the connector 306b-2. Further, a control signal is transmitted to the PIN diode 307-1 for switching the tuning capacitor 308-1 from the second line 506-2 through the connector 505b-5 and the connector 306b-3.

Third Embodiment

Figure 19:
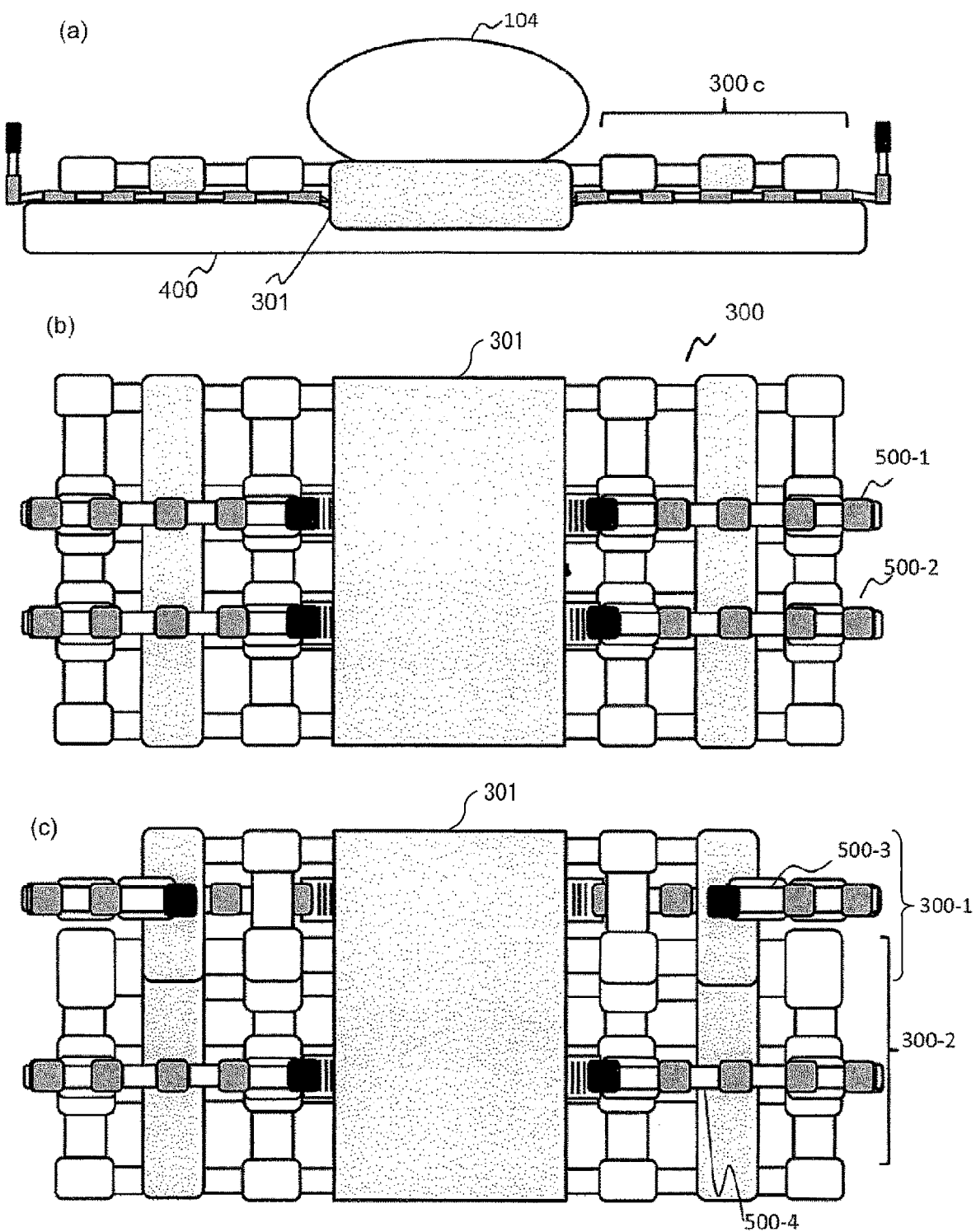
FIG. 19(a) is a sectional view illustrating an RF coil according to a third embodiment of the invention.
FIG. 19(b) is a plan view thereof.
FIG. 19(c) is a plan view illustrating a modification example of the RF coil of the third embodiment.

FIG. 19 shows a RF coil 300 of a third embodiment, in which FIG. 19(a) is a sectional view thereof, and FIG. 19(b) is a plan view (top view). The RF coil 300 of the third embodiment is a two-dimensional array type coil in which coil elements are arranged in a transverse direction and in a body length direction of a subject. The shown coil is an array type coil (3 columns and 8 rows) in which eight coil elements are arranged in a row direction (8 rows) and three of these are arranged in a column direction (3 columns). Similar to the first embodiment, a portion covered with a resin case 301 of the RF coil 300 is fixed to a patient table 400, but a portion other than the covered portion may be used to be wound around a subject 104. That is, a coil array portion 300c of the RF coil 300 is flexible. Belt-shaped fixtures 500-1 and 500-2 are respectively provided on both sides at two positions in the body length direction, and fix the RF coil 300 wound around the subject 104 from outside. The third embodiment is the same as the previous embodiments in that a fixture-side connector is provided in the fixtures 500-1 and 500-2, and an RF coil-side connector is provided in the RF coil 300, the shape (whether it is a wound shape or not) of the RF coil 300 is determined according to whether the fixture-side connector and the RF coil-side connector are fitted to each other, and a matching circuit or a tuning circuit of a coil element is automatically switched. A detection mechanism of the fitting may employ any one of a detection mechanism using turning on or off of a contact provided in the RF coil-side connector as in the first embodiment and a coaxial connector switch that transmits a control signal from a fixture-side interconnection to the RF coil as in the second embodiment, and in both cases, the same effects can be obtained. As in this embodiment, when coils corresponding to three columns are wound around a subject all at once, a circuit control based on connector connection of the invention may be performed with respect to coils in one column among three columns using one or more fixture belts.

On the other hand, FIG. 19(c) shows a modification example of the third embodiment. In this modification example, a flexible coil is divided into a first portion 300-1 that forms an array (1 column and 6 rows) in which six coil elements are arranged, and a second portion 300-2 that forms an array (2 columns and 8 rows) in which eight coil elements are arranged in two columns (2 columns). For example, the array coil of the first portion 300-1 is wound around the neck, and the array coil of 2 columns and 8 rows of the second portion 300-2 is wound around the body, for example. That is, both the array coils perform imaging in independent shapes. Accordingly, fixtures 500-3 and 500-4 are provided in the respective arrays 300-1 and 300-2. In the case of this modification example, a mechanism that detects a shape change by connector connection to perform a circuit control is provided in each of the first portion (300-1) and the second portion (300-2) capable of being independently changed in the shape.

As described above, in the array coil arranged in the two-dimensional array shape, similarly, optimal coil parameters (capacitor values of the matching circuit and the tuning circuit) are constantly selected according to a coil shape in imaging, and thus, it is possible to constantly realize an RF reception coil with high sensitivity or a flexible RF transmission/reception coil with high emission efficiency.

Fourth Embodiment

Figure 20:
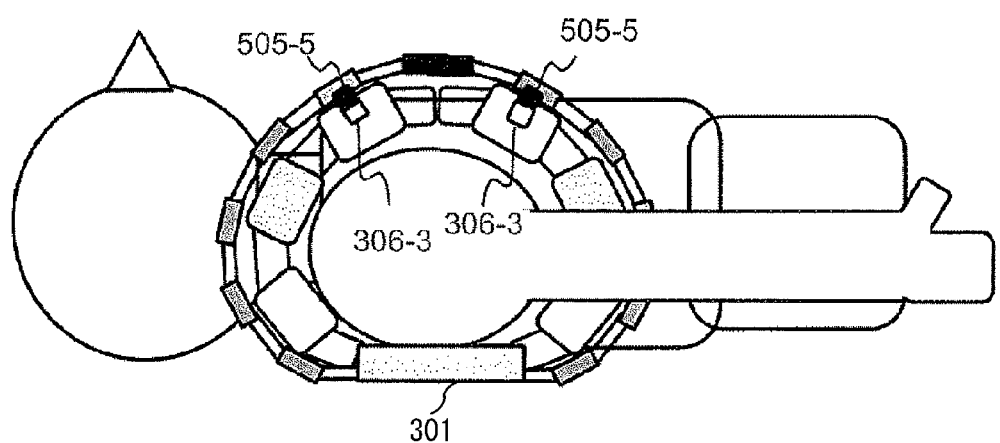
FIG. 20(a) is a partial sectional view illustrating a first use state of an RF coil for shoulder (joint) imaging according to a fourth embodiment of the invention.
FIG. 20(b) is a partial sectional view illustrating a second use state (photographing in an ABER state).
Figure 20:
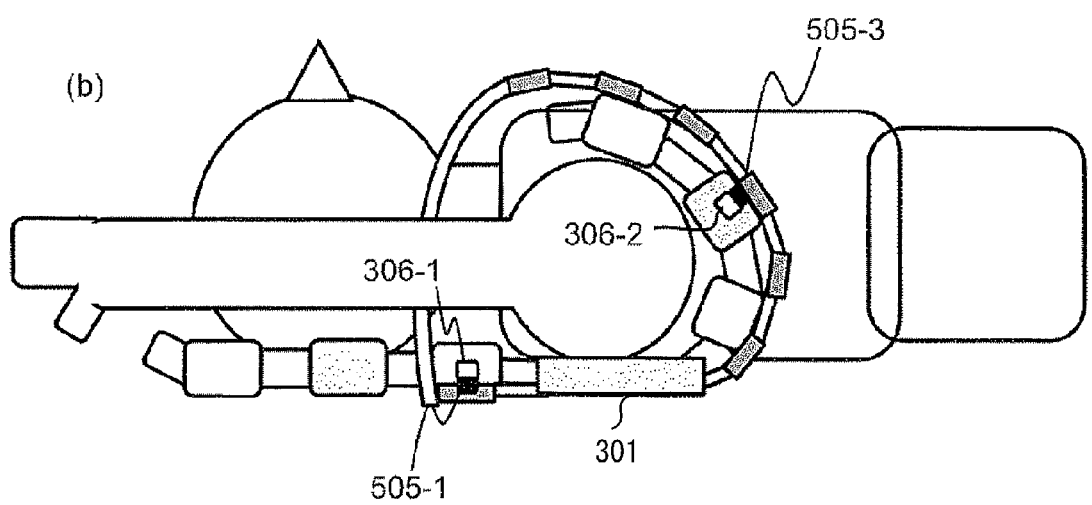

FIG. 20 shows a fourth embodiment of the invention. The fourth embodiment relates to a reception exclusive flexible RF coil or a transmission/reception flexible RF coil for imaging a shoulder joint. FIG. 20(a) is a diagram illustrating normal shoulder arthrography, and FIG. 20(b) is a diagram illustrating shoulder arthrography in a state where an arm is raised, which is referred to as an ABER posture. In this way, in the arthrography, the posture may be changed for imaging, but according to a flexible RF coil 300 of this embodiment, an optimal matching state and an optimal tuned state are permanently provided with respect to any posture. In FIG. 20(a), similar to the above-described embodiments, the right and left flexible portions are wound around the shoulder of the subject in a symmetrical form, in which a coil-side connector 306-3 and a fixture-side connector 505-5 are connected to each other. In FIG. 20(b), the right flexible portion is wound around the shoulder, and the tip of a fixture 500 is fixedly held in this state. A coil-side connector 306-2 and a fixture connector 505-3 are connected to each other. The left flexible portion is flatly extended, in which a coil-side connector 306-1 and a fixture connector 505-1 are connected to each other. In this way, the RF coil 300 may be used in a left-right asymmetric form. In such a case, similarly, it is obvious that an optimal matching capacitor and an optimal tuning capacitor are obtained in advance in each state, a connection state of connectors is determined corresponding to each coil shape, and a tuning switch circuit and a matching switch circuit are combined so as to have an optimal matching capacitor or an optimal tuning capacitor in each state, and thus, it is possible to constantly realize optimal coil parameters.

REFERENCE SIGNS LIST

100 GANTRY (PORTION SURROUNDED BY DOT LINE)
101 MAGNET
102 GRADIENT MAGNETIC FIELD GENERATION COIL
103 RADIO FREQUENCY TRANSMITTING COIL
104 SUBJECT
105 RECEIVER
106 RADIO FREQUENCY (RF) MAGNETIC FIELD GENERATOR
107 GRADIENT MAGNETIC FIELD POWER SOURCE
108 STORAGE MEDIUM
109 DISPLAY DEVICE
110 SEQUENCER
111 CALCULATOR
112 GANTRY MONITOR
200 TABLE COIL CONTROLLER
300 FLEXIBLE RF COIL
301, 302, 303, 304, 303-1 TO 303-3, 304-1 TO 304-3 RESIN CASE
306, 306-1 TO 306-3, 306b, 306b-1 TO 306b-3 RF COIL-SIDE CONNECTOR
307-1, 307b-1 TUNING SWITCH CIRCUIT
307-2, 307b-2 MATCHING SWITCH CIRCUIT
308-1 TO 308-5 TUNING CAPACITOR
309-1, 309-2 MATCHING CAPACITOR
311 TRANSMISSION/RECEPTION SWITCH
312 PRE-AMPLIFIER
313 POWER AMPLIFIER
314 TRANSMITTER
321-1 TO 321-3 PIN DIODE
331 TO 338 COIL ELEMENT
400 PATIENT TABLE
500 PATIENT FIXTURE
501 PATIENT FIXTURE CONNECTOR
502 PATIENT FIXTURE FLEXIBLE PORTION
503 PATIENT FIXTURE CONNECTING PORTION (ADJUSTER)
504 PATIENT FIXTURE FLEXIBLE PORTION
505, 505-1 TO 505-6, 505b, 505b-1 TO 505b-6 FIXTURE-SIDE CONNECTOR
506 FLEXIBLE MULTI-LAYER SUBSTRATE
506-1 TO 506-3 RECIPROCATING (BOTH WAY) LINE
510 FIRST TERMINAL OF FIXTURE-SIDE CONNECTOR
511 SECOND TERMINAL OF FIXTURE-SIDE CONNECTOR
512 THIRD TERMINAL OF FIXTURE-SIDE CONNECTOR
513 HOUSING OF FIXTURE-SIDE CONNECTOR

The invention claimed is:

1. A magnetic resonance imaging device, comprising:
a gantry that is provided with a static magnetic field generator that generates a static magnetic field and a gradient magnetic field generation coil that generates a gradient magnetic field;
a table that is disposed in the gantry and on which a test object is placed;
an RF coil that is configured so that a part thereof is fixed to the gantry or the table and at least another part thereof is formed of a flexible material and is deformable to be in contact with the test object, and receives a nuclear magnetic resonance signal generated from the test object;
a fixture that fixes the RF coil to the test object; and
a detector that detects the shape of the RF coil,
wherein the RF coil includes a matching switch circuit and a tuning switch circuit configured to change a matching constant and a tuning constant of the RF coil according to an output of the detector and configured to be in an optimal matching state and an optimal tuned state when the test object is placed on the RF coil in a state where the RF coil is flatly mounted on the table,
wherein the detector includes an RF coil-side connector disposed ancillary to the RF coil, a fixture-side connector disposed ancillary to the fixture, and a mechanism switch that turns on or off a connection between terminals when the RF coil-side connector and the fixture-side connector are connected to each other, and wherein the matching switch circuit and the tuning switch circuit have a circuit configuration that varies according to whether the mechanism switch turns the connection on or off, and respectively switch the matching switch circuit and the tuning switch circuit into the optimal matching state and the optimal tuned state in a shape of the RF coil corresponding to each of on the on state and the off state of the mechanism switch.

2. The magnetic resonance imaging device according to claim 1, wherein the fixture-side connector is provided in a plurality, and the mechanism switch includes a switching button pressed when the RF coil-side connector is fitted to any one of the plurality of fixture-side connectors, and a switch that turns on or off the connection between the terminals by the switching button.

3. The magnetic resonance imaging device according to claim 1, wherein the RF coil is a RF coil used both as a transmission coil and a reception coil that emits a radio frequency magnetic field to the test object and receives the nuclear magnetic resonance signal.

4. The magnetic resonance imaging device according to claim 1, wherein the part of the RF coil fixed to the table is fixed in the table.

5. The magnetic resonance imaging device according to claim 1, wherein the fixture has an end thereof which is fixed to the table.

6. A magnetic resonance imaging device, comprising:

a gantry that is provided with a static magnetic field generator that generates a static magnetic field and a gradient magnetic field generation coil that generates a gradient magnetic field;

a table that is disposed in the gantry and on which a test object is placed;

an RF coil that is configured so that a part thereof is fixed to the gantry or the table and at least another part thereof is formed of a flexible material and is deformable to be in contact with the test object, and receives a nuclear magnetic resonance signal generated from the test object;

a fixture that fixes the RF coil to the test object; and a detector that detects the shape of the RF coil, wherein the RF coil includes a matching switch circuit and a tuning switch circuit configured to change a matching constant and a tuning constant of the RF coil according to an output of the detector and configured to be in an optimal matching state and an optimal tuned state when the test object is placed on the RF coil in a state where the RF coil is flatly mounted on the table, wherein the detector includes an RF coil-side connector disposed ancillary to the RF coil, a fixture-side connector disposed ancillary to the fixture, and a mechanism switch that turns on or off a connection between terminals when the RF coil-side connector and the fixture-side connector are connected to each other, wherein the detector includes a coaxial switch connector that transmits a control voltage supplied through an interconnection of the fixture when the RF coil-side connector and the fixture-side connector are connected to each other, and wherein the matching switch circuit and the tuning switch circuit have a circuit configuration that varies according to the control voltage transmitted from the coaxial switch connector, and respectively switch the matching switch circuit and the tuning switch circuit into an optimal matching state and an optimal tuned state in a shape of the RF coil corresponding to a connection state of the RF coil-side connector and the fixture-side connector.

7. The magnetic resonance imaging device according to claim 6, wherein the matching switch circuit and the tuning switch circuit respectively include a PIN diode of which an on or off state is changed by the control voltage transmitted from the coaxial switch connector.

8. The magnetic resonance imaging device according to claim 6, wherein the plurality of coaxial switch connectors are arranged on a surface of the fixture, and a flexible interconnect substrate in which a plurality of reciprocating lines through which a control voltage is guided to at least a part of the plurality of coaxial switch connectors from a power source device is formed is arranged in the fixture.

* * * * *